United States Patent
Vallier et al.

(10) Patent No.: US 9,790,470 B2
(45) Date of Patent: Oct. 17, 2017

(54) IN VITRO PANCREATIC DIFFERENTIATION OF PLURIPOTENT MAMMALIAN CELLS

(71) Applicant: Cambridge Enterprise Limited, Cambridge, Cambridgeshire (GB)

(72) Inventors: Ludovic Vallier, Cambridge (GB); Hsin-hua Cho, Taipei (CN)

(73) Assignee: Cambridge Enterprise Limited, Cambridge (GB)

( * ) Notice: Subject to any disclaimer, the term of this patent is extended or adjusted under 35 U.S.C. 154(b) by 124 days.

(21) Appl. No.: 14/429,869

(22) PCT Filed: Sep. 16, 2013

(86) PCT No.: PCT/EP2013/069188
§ 371 (c)(1),
(2) Date: Jul. 6, 2015

(87) PCT Pub. No.: WO2014/044646
PCT Pub. Date: Mar. 27, 2014

(65) Prior Publication Data
US 2015/0225698 A1    Aug. 13, 2015

(30) Foreign Application Priority Data
Sep. 20, 2012 (GB) ................... 1216796.1

(51) Int. Cl.
*C12N 5/071* (2010.01)
*A61K 35/39* (2015.01)
*C12Q 1/68* (2006.01)
*G01N 33/50* (2006.01)
*G01N 33/74* (2006.01)

(52) U.S. Cl.
CPC ............ *C12N 5/0678* (2013.01); *A61K 35/39* (2013.01); *C12N 5/0676* (2013.01); *C12Q 1/6881* (2013.01); *G01N 33/507* (2013.01); *G01N 33/5038* (2013.01); *G01N 33/74* (2013.01); *C12N 2500/30* (2013.01); *C12N 2500/38* (2013.01); *C12N 2501/115* (2013.01); *C12N 2501/117* (2013.01); *C12N 2501/155* (2013.01); *C12N 2501/16* (2013.01); *C12N 2501/40* (2013.01); *C12N 2501/41* (2013.01); *C12N 2506/02* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| 2006/0040387 A1* | 2/2006 | Fisk | A01N 65/00 435/370 |
| 2010/0255580 A1* | 10/2010 | Rezania | C12N 5/0606 435/377 |
| 2011/0091971 A1* | 4/2011 | Davis | C12N 5/0603 435/377 |

FOREIGN PATENT DOCUMENTS

| EP | 2 233 566 | 9/2010 |
| WO | 2010091241 | 8/2010 |
| WO | 2012025725 A1 | 3/2012 |
| WO | 2012170853 | 12/2012 |

OTHER PUBLICATIONS

D'Amour et al., Nature Biotechnology 2006, 24:1392-1401.*
Xu et al., "Activin, BMP and FGF pathways cooperate to promote endoderm and pancreatic lineage cell differentiation from human embryonic stem cell", Mechanisms of Development, vol. 128, No. 7, pp. 412-427, Aug. 4, 2011.
Chng et al., "Activin/nodal signaling and pluripotency", Vitamins and Hormones, vol. 85, pp. 39-58, Jan. 1, 2011.
Lima et al., "Pancreatic Transcription Factors Containing Protein Transduction Domains Drive Mouse Embryonic Stem Cells towards Endocrine Pancreas", PLOS One, vol. 7, No. 5, e36481, May 2012.
International Search Report and Written Opinion in International Application No. PCT/EP2013/069188 dated Nov. 4, 2013.

* cited by examiner

Primary Examiner — Doug Schultz
(74) Attorney, Agent, or Firm — Greenberg Traurig, LLP; Fang Xie

(57) ABSTRACT

This invention relates to the in vitro differentiation of pluripotent cells into pancreatic progenitors by i) culturing pluripotent cells in a definitive endoderm (DE) medium comprising a TGFβ ligand, fibroblast growth factor (FGF), bone morphogenetic protein (BMP), a PI3K inhibitor and optionally a GSK3 β inhibitor to produce a population of definitive endoderm cells, ii) culturing the definitive endoderm cells in a first pancreatic medium comprising an activin antagonist; FGF; retinoic acid; and a BMP inhibitor to produce a population of dorsal foregut cells; iii) culturing the dorsal foregut cells in a second pancreatic medium comprising FGF, retinoic acid, a BMP inhibitor, and a hedgehog signalling inhibitor, and; iv) culturing the endoderm cells in a third pancreatic medium comprising FGF. The progenitor cells thus produced may be further differentiated into pancreatic endocrine cells. These methods may be useful, for example, in producing pancreatic cells for therapy or disease modelling.

39 Claims, 17 Drawing Sheets

IN VITRO PANCREATIC DIFFERENTIATION OF PLURIPOTENT MAMMALIAN CELLS

CROSS-REFERENCE TO RELATED APPLICATIONS

This application is a national phase application of International Application No. PCT/EP2013/069188 filed Sep. 16, 2013, which claims priority to and the benefit of GB1216796.1 filed Sep. 20, 2012, the disclosures of each of which applications are hereby incorporated herein in their entirety.

This invention relates to the in vitro induction of pancreatic differentiation in pluripotent mammalian cells.

The production of pancreatic beta cells represents a major objective for regenerative medicine. Indeed, large supply of these cells will enable the development of cell based therapy against diabetes, which is currently limited by the lack of donated organs and difficulty to expand insulin secreting cells in vitro. Human pluripotent stem cells (hPSCs) of embryonic origin (human Embryonic Stem Cells or hESCs) [1] or generated from reprogrammed somatic cells (human Induced pluripotent Stem Cells or hIPSCs) [2] offer the prospects of bypassing these restrictions. Indeed, these cells are capable of proliferating indefinitely in vitro while maintaining the capacity to differentiate into a broad number of cell types including pancreatic progenitors [3-6]. However, robust protocols allowing for the production of homogenous population of these cells in defined culture conditions have not yet been established. Indeed, available methods contain undefined animal products, such as feeders, foetal bovine serum (FBS) and Matrigel.

Furthermore, they only allow for the generation of heterogeneous populations of cells, thus increasing the risk of teratoma formation after transplantation [7, 8]. They also appear to work efficiently only on a limited number of hPSC lines [3] which hinders their use in a broad number of laboratories.

Most of the culture systems currently used to direct differentiation of hPSCs mimic normal development since this approach could facilitate the generation of fully functional cell types. Consequently, the knowledge coming from studies on mice or other vertebrate animal models has been used to inform strategies driving human hPSCs towards specific lineages.

The pancreas and the liver arise at around embryonic day 8.5 to 9.5 from adjacent regions of the developing primitive foregut under the influence of inductive signals which are secreted by the nearby mesoderm [9]. These signals are likely to command the expression of transcription factors necessary for pancreatic specification such as HXLB9, which marks the dorsal foregut prior to the formation of the pancreatic bud [10, 11] and PDX1 which marks regions of the foregut from which ventral and dorsal pancreatic buds arise [12, 13].

The newly specified pancreatic progenitor quickly expresses additional markers including PTF1A, NKX6.1 and SOX9 and these progenitors give rise to both endocrine (islets of Langerhans) and exocrine (acinar and ductal cells) cells of the pancreas. Similar mechanisms control hepatic specification although they involve different set of transcription factors such as HEX, GATA6, PROX1 and HNF4α [14] and signalling pathways such as BMP and FGFs [15]. Despite this broad knowledge, the molecular mechanisms enabling extracellular signalling pathways to orchestrate the transcriptional networks characterising pancreatic or hepatic progenitors remain to be elucidated especially in human and hPSCs could present unique advantages to complete this major task.

This invention relates to a process for the high efficiency in vitro differentiation of pluripotent cells into pancreatic progenitor and pancreatic endocrine cells. This may be useful, for example, in producing pancreatic cells for cell-based therapies or disease modelling.

An aspect of the invention provides a method for producing a population of pancreatic progenitor cells which comprises:
  i) providing a population of pluripotent cells;
  ii) culturing the population in a definitive endoderm (DE) induction medium to produce a population of definitive endoderm cells, wherein said DE induction medium comprises a TGFβ, ligand, fibroblast growth factor (FGF), bone morphogenetic protein (BMP), a PI3K inhibitor and optionally a GSK3β inhibitor;
  iii) culturing the population of definitive endoderm cells in a first pancreatic induction medium comprising an activin antagonist; FGF; retinoic acid; and a BMP inhibitor to produce a population of dorsal foregut cells;
  iv) culturing the dorsal foregut cells in a second pancreatic induction medium comprising FGF, retinoic acid, a BMP inhibitor, and a hedgehog signalling inhibitor;
  v) culturing the endoderm cells in a third pancreatic induction medium comprising FGF;
  thereby producing a population of pancreatic progenitor cells.

The pancreatic progenitor cells may be further differentiated into pancreatic endocrine cells. For example, a method may further comprise;
  (vi) culturing the population of pancreatic progenitor cells in a first endocrine induction medium and a second endocrine induction medium to produce a population of pancreatic endocrine cells.

A pluripotent cell is a cell which exhibits an undifferentiated phenotype and is potentially pluripotent i.e. it is capable of differentiating into any foetal or adult cell type of any of the three germ layers (endoderm, mesoderm and endoderm). A pluripotent cell is distinct from a totipotent cell and cannot give rise to extraembryonic cell lineages. Pluripotent cells may express one or more of the following pluripotency associated markers: Oct4, Sox2, Alkaline Phosphatase, POU5f1, SSEA-3, Nanog, SSEA-4, Tra-1-60, KLF-4 and c-myc, preferably POU5f1, NANOG and SOX2. A human pluripotent cell may lack markers associated with specific differentiative fates, such as Bra, Sox17, FoxA2, αFP, Sox1, NCAM, GATA6, GATA4, Hand1 and CDX2.

Pluripotent cells may be mammalian cells, preferably human cells.

The population of pluripotent cells may be clonal i.e. genetically identical cells descended from a single common ancestor cell.

A population of pluripotent cells suitable for use in the present methods may be substantially free from one or more other cell types. Pluripotent cells may, for example, be separated from other cell types, using any technique known to those skilled in the art, including those based on the recognition of extracellular epitopes by antibodies and magnetic beads or fluorescence activated cell sorting (MACS or FACS) including the use of antibodies against extracellular regions of molecules found on stem cells, such as SSEA4.

Pluripotent cells may include embryonic stem cells (ESCs), foetal and adult somatic stem cells and iPS cells.

Suitable embryonic stem cells may be obtained using conventional techniques. For example, ESCs cells may be obtained from a cultured ESC cell line, for example a hESC line. Numerous cultured hESC lines are publically available from repositories (e.g. NIH Human Embryonic Stem Cell Registry), such as CHB-1 to CHB-12, RUES1 to RUES3, HUES1 to HUES28, HUES45, HUES48, HUES49, HUES53, HUES62 to HUES66, WA01 (H1), WA07 (H7), WA09 (H9), WA13 (H13), WA14 (H14), NYUES1 to NYUES7, MFS5, and UCLA1 to UCLA3. Further examples of suitable human embryonic stem cell lines are described in (Thomson J A et al Science 282: 1145-1147 (1998); Reubinoff et al. Nat Biotechnol 18:399-404 (2000); Cowan, C. A. et al. N. Engl. J. Med. 350, 1353-1356 (2004), Gage, F. H., et al. Ann. Rev. Neurosci. 18 159-192 (1995); and Gotlieb (2002) Annu. Rev. Neurosci 25 381-407); Carpenter et al. Stem Cells. 5(1): 79-88 (2003). Potentially clinical grade hESCs are described in Klimanskaya, I. et al. Lancet 365, 1636-1641 (2005) and Ludwig, T. E. et al. Nat. Biotechnol. 24, 185-187 (2006).

Suitable hESCs may be obtained without destroying a human embryo.

In other embodiments, the pluripotent cells are not hESCs, and may, for example, be fetal or adult somatic stem cells or iPS cells, preferably human iPS cells.

iPS cells are pluripotent cells which are derived from non-pluripotent, fully differentiated ancestor cells. Suitable ancestor cells include adult fibroblasts and peripheral blood cells. Ancestor cells are typically reprogrammed by the introduction of pluripotency genes or proteins, such as Oct4, Sox2 and Sox1 into the cell. The genes or proteins may be introduced into the differentiated cells by any suitable technique, including plasmid or more preferably, viral transfection or direct protein delivery. Other genes, for example Kif genes, such as Kif-1, -2, -4 and -5; Myc genes such as C-myc, L-myc and N-myc; nanog; and Lin28 may also be introduced into the cell to increase induction efficiency. Following introduction of the pluripotency genes or proteins, the ancestor cells may be cultured. Cells expressing pluripotency markers may be isolated and/or purified to produce a population of iPS cells. Techniques for the production of iPS cells are well-known in the art (Yamanaka et al Nature 2007; 448:313-7; Yamanaka 6 2007 Jun. 7; 1(1): 39-49; Kim et al Nature. 2008 Jul. 31; 454(7204):646-50; Takahashi Cell. 2007 Nov. 30; 131(5):861-72. Park et al Nature. 2008 Jan. 10; 451(7175):141-6; Kimet et al Cell Stem Cell. 2009 Jun. 5; 4(6):472-6; Vallier, L., et al. Stem Cells, 2009. 9999(999A): p. N/A).

iPS cells may be derived from cells, such as fibroblasts, obtained from an individual without a genetic disorder. iPS cells derived from an individual without a genetic disorder may be used as described herein to produce pancreatic progenitor and pancreatic endocrine cells with a normal (i.e. non-disease associated) genotype.

iPS cells may be derived from cells, such as fibroblasts, obtained from individuals with distinct genetic backgrounds. For example, iPS cells may be produced from cells from individuals having a pancreatic condition, for example a diabetic condition such as type 1 and type 2 diabetes, individuals having a high risk of a pancreatic condition and/or individuals with a low risk of a pancreatic condition. Pancreatic cells produced as described herein from individuals with distinct genetic backgrounds may be useful in studying the mechanisms of pancreatic conditions, such as diabetes, and identifying therapeutic targets iPS cells may be derived from cells, such as fibroblasts, obtained from an individual with a genetic disorder, for example a genetic disorder affecting pancreatic development and/or associated with pancreatic dysfunction, including diabetic conditions such as type 1 and type 2 diabetes, pancreatic agenesis, hereditary pancreatitis, familial pancreatitis, Schwachman-Diamond syndrome, and pancreatic cancer or a genetic disorder which has pancreatic symptoms or complications. Genetic disorders may include monogenetic disorders.

Any cell with the genotype of the disorder, for example a genetic mutation or defect, may be used to produce iPS cells, although samples of fibroblasts, e.g. dermal fibroblasts, may be conveniently obtained.

iPS cells which are produced from cells obtained from an individual with a genetic disorder, for example a genetic disorder affecting pancreatic development and/or associated with pancreatic dysfunction, may be used as described herein to produce pancreatic cells which have the genotype of the genetic disorder. Typically, the pancreatic cells will contain the genetic mutation or defect which is associated with the genetic disorder. These cells may be useful in treating patients with the genetic disorder as described above or the modelling of pancreatic diseases, including diabetic conditions.

Pluripotent cells may be obtained from pluripotent cell lines using conventional techniques (Vallier, L. et al Dev. Biol, 275, 403-421 (2004), Cowan, C. A. et al. N. Engl. J. Med. 350, 1353-1356 (2004), Joannides, A. et al. Stem Cells 24, 230-235 (2006) Klimanskaya, I. et al. Lancet 365, 1636-1641 (2005), Ludwig, T. E. et al. Nat. Biotechnol. 24, 185-187 (2006)) Pluripotent cells for use in the present methods may be grown in defined conditions or on feeder cells. For example, pluripotent cells may be conventionally cultured in a culture dish on a layer of feeder cells, such as irradiated mouse embryonic fibroblasts (MEF), at an appropriate density (e.g. $10^5$ to $10^6$ cells/60 mm dish), or on an appropriate substrate with feeder conditioned or defined medium. Pluripotent cells for use in the present methods may be passaged by enzymatic or mechanical means. Suitable culture media for pluripotent cells include Knockout Dulbecco's Modified Eagle's Medium (KO-DMEM) supplemented with 20% Serum Replacement, 1% Non-Essential Amino Acids, 1 mM L-Glutamine, 0.1 mM β-mercaptoethanol and 4 ng/ml to 10 ng/ml FGF2.

Other suitable culture media for pluripotent cells include Knockout (KS) medium supplemented with 4 ng/ml FGF2; Knockout Dulbecco's Modified Eagle's Medium (KO-DMEM) supplemented with 20% Serum Replacement, 1% Non-Essential Amino Acids, 1 mM L-Glutamine, 0.1 mM β-mercaptoethanol and 4 ng/ml to 10 ng/ml human FGF2; and DMEM/F12 supplemented with 20% knockout serum replacement (KSR), 6 ng/ml FGF2 (PeproTech), 1 mM L-Gln, 100 μm non-essential amino acids, 100 μM 2-mercaptoethanol, 50 U/ml penicillin and 50 mg/ml streptomycin.

In preferred embodiments, a population of pluripotent cells for use in the present methods may be cultured in chemically defined medium (CDM) with activin A (10 ng/mL) and FGF2 (20 ng/mL) to maintain pluripotency before differentiation is induced as described below (Vallier et al., 2005). Pluripotent cells may be harvested using collagenase-free reagents, for example Accutase™ (Bio-West).

In some embodiments, the pluripotent cells may comprise a reporter, preferably a fluorescent reporter, which is operably linked to a tissue-specific promoter (i.e. a pancreatic specific promoter). Following differentiation into pancreatic progenitors or pancreatic endocrine cells as described herein, cells which express the reporter may be isolated and/or purified from other cell types, for example by fluorescence activated cell sorting (FACS).

The pluripotent cells may be differentiated into pancreatic progenitor cells in a four step process. First, the population of pluripotent cells is induced to differentiate into a population of definitive endoderm (DE) cells. The DE cells are then induced to differentiate into dorsal foregut cells, which are induced in two steps to differentiate into pancreatic progenitor cells.

The extent of differentiation of the cell population during each step may be determined during cell culture by monitoring and/or detecting the expression of one or more cell markers in the population of differentiating cells. For example, an increase in the expression of markers characteristic of the more differentiated cell type or a decrease in the expression of markers characteristic of the less differentiated cell type may be determined. The expression of cell markers may be determined by any suitable technique, including immunocytochemistry, immunofluorescence, RT-PCR, immunoblotting, fluorescence activated cell sorting (FACS), and enzymatic analysis.

After each step, the population of partially differentiated cells which is produced by that step may be substantially free from other cell types. For example, the population may contain 85% or more, 90% or more, 95% or more, or 98% or more partially differentiated cells, following culture in the medium. Preferably, the population of cells is sufficiently free of other cell types that no purification is required. If required, the population of partially differentiated cells may be purified by any convenient technique, such as FACS.

A population of partially differentiated cells produced by a step in the methods described herein may be cultured, maintained or expanded before the next differentiation step. Partially differentiated cells may be expanded by any convenient technique.

The induction of differentiation at each step involves culturing of cells in a chemically defined medium (CDM), preferably humanised CDM, which is supplemented with a set of differentiation factors which induce the cells to undertake the differentiation step. The set of differentiation factors listed for each medium is preferably exhaustive and medium may be devoid of other differentiation factors.

A chemically defined medium (CDM) is a nutritive solution for culturing cells which contains only specified components, preferably components of known chemical structure. A CDM is devoid of undefined components or constituents which include undefined components, such as feeder cells, stromal cells, serum, matrigel, serum albumin and complex extracellular matrices. Preferably, the chemically defined medium is humanised. A humanised chemically defined medium is devoid of components or supplements derived from non-human animals, such as Foetal Bovine Serum (FBS), Bovine Serum Albumin (BSA), and mouse feeder cells. Conditioned medium includes undefined components from cultured cells and is not chemically defined.

Suitable chemically defined basal media include Advanced Dulbecco's modified eagle medium (DMEM) (Price et al Focus (2003) 25 3-6). Advanced DMEM is well-known in the art and readily available from commercial sources (e.g. Life Technologies, USA). The components of Advanced DMEM are shown in Table 1. In some preferred embodiments, Advanced DMEM may be employed as the basal medium in the pancreatic induction media described herein.

Other suitable chemically defined basal media include CDM-PVA (Johansson and Wiles (1995) Mol Cell Biol 15, 141-151) which is supplemented with polyvinyl alcohol, insulin, transferrin and defined lipids. Johansson and Wiles CDM consists of: 50% IMDM (Gibco) plus 50% F12 NUT-MIX (Gibco); 7 µg/ml insulin; 15 µg/ml transferrin; 1 mg/ml polyvinyl alcohol (PVA; 1% chemically defined lipid concentrate (Invitrogen); and 450 µM 1-thiolglycerol. In some preferred embodiments, CDM-PVA may be employed in the endoderm induction medium described herein.

Other suitable chemically defined basal media include RPMI-1640 (Moore, G. E. and Woods L. K., (1976) Tissue Culture Association Manual. 3, 503-508). In some preferred embodiments, RPMI-1640 may be employed in the anterior definitive endoderm induction medium described herein.

Other suitable chemically defined basal medium are known in the art and available from commercial sources (e.g. Sigma-Aldrich MI USA; Life Technologies USA).

Chemically defined basal media suitable for use as described herein may comprise a serum-free media supplement (i.e. a supplemented basal media). Suitable serum-free media supplements include B27 and NS21 and are described elsewhere herein. Preferably the media described herein are serum-free. The use of serum-free conditions and the absence of animal products facilitate scale-up for clinical applications.

A chemically defined basal medium, such as CDM/PVA, RPMI-1640 or Advanced DMEM, may be supplemented with a specified set of differentiation factors to produce an endoderm or pancreatic induction medium, or endocrine induction as described herein.

Differentiation factors are factors which modulate, for example promote or inhibit, a signalling pathway which mediates differentiation in a mammalian cell. Differentiation factors may include growth factors and inhibitors which modulate one or more of the Activin/Nodal, FGF, Wnt or BMP signalling pathways. Differentiation factors which are proteins are preferably recombinant human factors.

Examples of differentiation factors include FGF2, BMP4, retinoic acid, TGF, GDF3, LIF, IL, activin and phosphatidylinositol 3-kinase (PI3K) inhibitors.

Differentiation factors which are used in one or more of the media described herein include TGFβ ligands, fibroblast growth factor (FGF), bone morphogenetic protein (BMP), PI3K inhibitors, activin/TGFβ antagonists; retinoic acid; BMP antagonists; hedgehog signalling inhibitors; notch signalling inhibitors and GSK3 beta inhibitors.

TGFβ ligands are peptides of the TGFβ superfamily which stimulate SMAD2 and SMAD3 mediated intracellular signalling pathways in mammalian cells. Members of the TGFβ superfamily possess a characteristic structure and are well-known in the art.

The TGFβ ligand may be Activin, TGFβ, Nodal or GDF3, preferably activin.

Activin (Activin A: NCBI GeneID: 3624 nucleic acid reference sequence NM_002192.2 GI: 62953137, amino acid reference sequence NP_002183.1 GI: 4504699) is a dimeric polypeptide which exerts a range of cellular effects via stimulation of the Activin/Nodal pathway (Vallier et al., Cell Science 118:4495-4509 (2005)). Activin is readily available from commercial sources (e.g. Stemgent Inc. MA USA). Conveniently, the concentration of Activin in a medium described herein may be from 10 to 1000 ng/ml, preferably about 100 ng/ml.

TGFβ (NCBI GeneID: 7040 nucleic acid reference sequence NM_000660.4 GI: 260655621, amino acid reference sequence NP_000651.3 GI: 63025222) is a homodimeric polypeptide which regulates proliferation and differentiation (Watabe, T. et al (2009). Cell Res. 19:103-115). Recombinant human TGFβ is readily available from commercial sources (e.g. Stemgent Inc. MA USA). Conveniently, the concentration of TGFβ in the medium may be from 10 to 1000 ng/ml, preferably about 100 ng/ml.

Nodal (NCBI GeneID 4838 nucleic acid sequence reference NM_018055.4 GI:222352097, amino acid sequence reference NP_060525.3 GI:222352098) is a member of the TGFbeta superfamily which regulates differentiation (Hamada et al Nat. Rev. Genet. 3 (2): 103-13). Nodal is readily available from commercial sources (e.g. Abcam Ltd, UK). Conveniently, the concentration of Nodal in the medium may be from 10 to 1000 ng/ml, preferably about 100 ng/ml.

GDF3 (NCBI Gene ID 9573 nucleic acid sequence reference NM_020634.1 GI:10190669, amino acid sequence reference NP_065685.1 GI:10190670) is a member of TGFβ superfamily which is characterized by a polybasic proteolytic processing site that is cleaved to produce a mature GDF3 protein containing seven conserved cysteine residues. Conveniently, the concentration of GDF3 in the medium may be from 10 to 1000 ng/ml, preferably about 100 ng/ml.

Fibroblast growth factor is a protein factor which stimulates cellular growth, proliferation and cellular differentiation by binding to a fibroblast growth factor receptor (FGFR). Suitable fibroblast growth factors include any member of the FGF family, for example any one of FGF1 to FGF14 and FGF15 to FGF23.

Preferably, the fibroblast growth factor is FGF2 (NCBI GeneID: 2247, nucleic acid sequence NM_002006.3 GI: 41352694, amino acid sequence NP_001997.4 GI: 41352695); FGF7 (also known as keratinocyte growth factor (or KGF), NCBI GeneID: 2247, nucleic acid sequence NM_002006.3 GI: 41352694, amino acid sequence NP_001997.4 GI: 41352695); or FGF10 (NCBI GeneID: 2247, nucleic acid sequence NM_002006.3 GI: 41352694, amino acid sequence NP_001997.4 GI: 41352695). Most preferably, the fibroblast growth factor is FGF10 (Amit, M., et al. *Developmental Biology* 227:271-278 (2000)). Conveniently, the concentration of FGF in a medium described herein may be from 1 to 500 ng/ml, for example, 10 to 150 ng/ml, 10 to 50 ng/ml or 5 to 25 ng/ml, preferably about 20 ng/ml.

Fibroblast growth factors, such as FGF2, FGF7 and FGF10, may be produced using routine recombinant techniques or obtained from commercial suppliers (e.g. R&D Systems, Minneapolis, Minn.; Stemgent Inc, USA).

In some embodiments, FGF may be replaced by epidermal growth factor (EGF; NCBI GeneID: 1950, nucleic acid sequence NM_001178130.1 GI: 296011012; amino acid sequence NP_001171601.1 GI: 296011013). Epidermal growth factor is a protein factor which stimulates cellular growth, proliferation and cellular differentiation by binding to a epidermal growth factor receptor (EGFR). EGF may be produced using routine recombinant techniques or obtained from commercial suppliers (e.g. R&D Systems, Minneapolis, Minn.; Stemgent Inc, USA).

Bone morphogenetic protein (BMP) Bone Morphogenic Proteins bind to Bone Morphogenic Protein Receptors (BMPRs) and stimulate intracellular signalling through pathways mediated by SMAD1, SMAD5 and SMAD9. Suitable Bone Morphogenic Proteins include any member of the BMP family, for example BMP2, BMP3, BMP4, BMP5, BMP6 or BMP7. Preferably the second TGFβ ligand is BMP2 (NCBI GeneID: 650, nucleic acid sequence NM_001200.2 GI: 80861484; amino acid sequence NP_001191.1 GI: 4557369) or BMP4 (NCBI GeneID: 652, nucleic acid sequence NM_001202.3 GI: 157276592; amino acid sequence NP_001193.2 GI: 157276593). Suitable BMP5 include BMP4. Conveniently, the concentration of a Bone Morphogenic Protein, such as BMP2 or BMP4 in a medium described herein may be from 1 to 500 ng/ml, preferably about 10 ng/ml.

Bone Morphogenic Proteins may be produced using routine recombinant techniques or obtained from commercial suppliers (e.g. R&D, Minneapolis, USA, Stemgent Inc, USA).

PI3K inhibitors inhibit the activity of phosphatidylinositol 3-kinases, such as phosphatidylinositol-4,5-bisphosphate 3-kinase (EC2.7.1.153).

Suitable PI3K inhibitors include wortmannin; LY301497 (17-b-hydroxywortmannin); LY294002 (2-morpholin-4-yl-8-phenylchromen-4-one: Maclean et al (2007) Stem Cells 25 29-38); CLB1309 (KN309: (±)-2-({1-[7-methyl-2-(morpholin-4-yl)-4-oxo-pyrido[1,2-a]pyrimidin-9-yl]ethyl}amino) benzoic acid); PX-866 ((1E,4S,4aR,5R,6aS,9aR)-5-(Acetyloxy)-1-[(di-2-propen-1-ylamino)methylene]-4,4a,5,6,6a,8,9,9a-octahydro-11-hydroxy-4-(methoxymethyl)-4a,6a-dimethylcyclopenta[5,6]naphtho[1,2-c]pyran-2,7,10(1H)-trione); IC87114 (quinolone pyrrolopyrimidine); GDC-0941 (2-(1H-Indazol-4-yl)-6-[[4-(methylsulfonyl)-1-piperazinyl] methyl]-4-(4-morpholinyl)-thieno[3,2-d]pyrimidine); TGX-221 (7-methyl-2-(4-morpholinyl)-9-[1-(phenylamino) ethyl]-4H-pyrido[1,2-a]pyrimidin-4-one), quercetin; BEZ235; XL147; X1765; PX-866; ZSTK474 (2-(2-difluoromethylbenzimidazol-1-yl)4,6-dimorpholino-1,3,5-triazine); and SF1126 (2-[2-methoxyethylamino]-8-phenyl-4H-1-benzopyran-4-one). Other PI3K inhibitors are available in the art.

In some preferred embodiments, the PI3K inhibitor is LY294002.

Suitable PI3K inhibitors may be obtained from commercial suppliers (e.g. Calbiochem CA USA).

For example, a medium may contain 1 to 100 μM PI3K inhibitor, such as LY294002, preferably about 10 μM.

An activin/TGFβ antagonist inhibits activin/Nodal signalling and promotes specification of foregut cells into pancreatic rather than hepatic lineages.

Suitable activin/TGFβ antagonists include SB431542 (4-(5-Benzol[1,3]dioxol-5-yl-4-pyridin-2-yl-1H-imidazol-2-yl)-benzamide hydrate; Sigma, Tocris Bioscience, Bristol UK; (Inman et al Mol Pharmacol (2002) 62 1 65-74), naringenin (5,7-dihydroxy-2-(4-hydroxyphenyl)chroman-4-one), SIS3 (6,7-Dimethoxy-2-((2E)-3-(1-methyl-2-phenyl-1H-pyrrolo[2,3-b]pyridin-3-yl)-prop-2-enoyl))-1,2,3,4-tetrahydroisoquinoline), A83-01 (3-(6-Methyl-2-pyridinyl)-N-phenyl-4-(4-quinolinyl)-1H-pyrazole-1-carbothioamide) and soluble protein factors, such as lefty (e.g. human lefty 2: NP_003231.2 GI:27436881), cerberus (e.g. human Cerberus 1: NP_005445.1 GI:4885135) or follistatin (e.g. human follistatin: NP_006341.1 GI:5453652). Preferably the activin/TGFβ antagonist is SB-431542.

Conveniently, the concentration of activin/TGFβ antagonist in a medium may be from 1 to 100 μM, preferably about 10 μM.

Retinoic acid (2E,4E,6E,8E)-3,7-dimethyl-9-(2,6,6-trimethylcyclohexen-1-yl)nona-2,4,6,8-tetraenoic acid) is a metabolite of vitamin A that modulates transcription through binding to the retinoic acid receptor (RAR) and modulates differentiation in a range of cell types. Preferably all-trans retinoic acid is employed in media described herein.

Conveniently, the concentration of retinoic acid in a medium may be 1 to 10 μM of preferably about 2 μM.

Retinoic acid is available from commercial suppliers (e.g. Sigma Aldrich, USA; Stemgent Inc, USA).

BMP antagonists inhibit BMP signalling in a cell. Various BMP antagonists are known in the art, including LDN-193189 (4-(6-(4-(piperazin-1-yl)phenyl)pyrazolo[1,5-a]pyrimidin-3-yl)quinoline; Yu et al (2008) Nat Chem Biol 4 33-41)), GDF3, Noggin, and dorsomorphin (6-[4-[2-(1-Piperidinyl)ethoxy]phenyl]-3-(4-pyridinyl)-pyrazolo[1,5-a] pyrimidine; Yu et al (2008) Nat Chem Biol 4 33-41)). Preferably the BMP antagonist is noggin.

Conveniently, the concentration of BMP antagonist in the medium may be from 1 to 1000 ng/ml, for example 10 to 1000 ng/ml, preferably about 50 ng/ml.

A hedgehog signalling inhibitor inhibits signalling through the hedgehog signalling pathway which is mediated by Sonic Hedgehog (SHH) and Smoothened (SMO). Suitable hedgehog signalling inhibitors are well known in the art and include 3-Keto-N-(aminoethyl-aminocaproyl-dihydrocinnamoyl)cyclopamine (KAAD-cyclopamine), saridegib, vismodegib and erismodegib. Preferably, the hedgehog signalling inhibitor is KAAD-cyclopamine. Conveniently, the concentration of hedgehog signalling inhibitor in the medium may be from 1 to 100 ng/ml, preferably about 50 ng/ml.

A Notch signalling inhibitor inhibits the passage of signals through the Notch signalling pathway which is mediated by Notch receptors, such as Notch-1 to Notch-4 in mammalian cells. Suitable Notch signalling inhibitors are well known in the art and include N—[N-(3,5-difluorophenacetyl)-1-alanyl]-S-phenylglycine t-butyl ester (DAPT).

Conveniently, the concentration of notch signalling inhibitor in the medium may be from 1 to 10 mM, preferably about 1 mM.

GSK3β, inhibitors inhibit the activity of glycogen synthase kinase 3β (Gene ID 2932: EC2.7.11.26). Suitable inhibitors include CHIR99021 (6-((2-((4-(2,4-Dichlorophenyl)-5-(4-methyl-1H-imidazol-2-yl)pyrimidin-2-yl)amino) ethyl)amino)nicotinonitrile; Ring D. B. et al., Diabetes, 52:588-595 (2003)) alsterpaullone, kenpaullone, SB216763 (3-(2,4-dichlorophenyl)-4-(1-methyl-1H-indol-3-yl)-1H-pyrrole-2,5-dione), and SB415286 (3-[(3-chloro-4-hydroxyphenyl)amino]-4-(2-nitrophenyl)-1H-pyrrole-2,5-dione).

For example, the endoderm induction medium may contain 0.3 to 30 µM of a GSK3β inhibitor, such as CHIR99021, preferably about 3 µM.

Suitable hedgehog signalling inhibitors, notch signalling inhibitors and GSK3β inhibitors are available from commercial suppliers (e.g. Stemgent Inc. MA USA; Cayman Chemical Co. MI USA).

The population of pluripotent cells is cultured in an endoderm induction medium to induce differentiation into DE cells. Suitable methods for the differentiation of hESCs and hIPSCs into near-homogenous populations of Definitive Endoderm (DE) cells are known in the art (Teo A K et al. (2011) Genes Dev 25: 238-250; WO2008/056166; WO2012/025725).

The endoderm induction medium may be a chemically defined medium (CDM) which comprises a TGFβ ligand, preferably activin, fibroblast growth factor (FGF), bone morphogenetic protein (BMP), a PI3K inhibitor and optionally a glycogen synthase kinase 3β inhibitor, preferably CHIR99021. In some embodiments, these may be the only differentiation factors in the medium.

In some embodiments, a single step process may be employed to induce pluripotent cells, such as ES cells, to differentiate into definitive endoderm (DE) cells. The process may comprise culturing cells in endoderm induction medium. Suitable methods and media are described in WO2008/056166. The endoderm induction medium may consist of a chemically defined basal medium, such as CDM-PVA or Advanced DMEM, supplemented with TGFβ ligand, preferably activin, (for example, 5 to 25 ng/ml, preferably about 10 ng/ml), FGF2 (for example 5 to 25 ng/ml, preferably about 20 ng/ml), BMP-4 (for example at 5 to 20 ng/ml, preferably about 10 ng/ml), a phosphatidylinositol 3-kinase inhibitor, preferably LY294002 (for example at 5-30 µM, preferably 5-10 µM).

The population of pluripotent cells may be cultured for 2 to 4 days, most preferably 3 days in the endoderm induction medium to produce the population of definitive endoderm cells.

In some embodiments, a three step process may be employed to induce pluripotent cells, such as iPS cells, to differentiate into definitive endoderm (DE) cells. The process may comprise culturing cells in endoderm induction medium with and then without GSK3β inhibitor, followed by culture in an ADE induction medium. Suitable methods and media are described in WO2012/025725. For example, differentiation of the population of pluripotent cells into DE cells may comprise;

(a) culturing the population of pluripotent cells in an endoderm induction medium as described above which is supplemented with a glycogen synthase kinase 3β inhibitor, preferably CHIR99021;

(b) further culturing the population in the endoderm induction medium without the glycogen synthase kinase 3β inhibitor, and, (c) further culturing the population in a ADE induction medium which comprises a TGFβ ligand and fibroblast growth factor activity to produce the population of definitive endoderm (DE) cells.

The cells may be incubated in each medium, for example for 12 to 36 hours, preferably about 24 hours.

The glycogen synthase kinase 3β inhibitor may be present in the medium in step (a) at 0.3-30 µM, preferably about 3 µM.

The Anterior Definitive Endoderm (ADE) induction medium may be a chemically defined medium (CDM) which comprises a TGFβ ligand, preferably activin, and a fibroblast growth factor (FGF). In some embodiments, these may be the only differentiation factors in the medium.

For example, a suitable ADE medium may consist of a chemically defined basal medium, for example RPMI-1640; a TGFβ ligand, preferably activin, (for example, 10 to 250 ng/ml, preferably about 100 ng/ml); and FGF, such as FGF2 (for example 5 to 500 ng/ml, preferably about 40 ng/ml). The chemically defined basal medium may be supplemented with a serum-free media supplement, such as B27 or NS21.

The population of definitive endoderm cells may express endoderm markers such as SOX17, CXCR4 and GSC and may lack expression of pluripotency markers or markers associated with ectodermal or mesodermal lineages. For example the definitive endoderm cells may not express at detectable levels one or more, preferably all, of the following; Oct4, Sox2, alkaline phosphatase, SSEA-3, Nanog, SSEA-4, Tra-1-60 and KLF-4.

The population of definitive endoderm cells is cultured in a series of pancreatic induction media to induce differentiation into pancreatic progenitor cells.

A first pancreatic induction medium is employed to induce the definitive endoderm cells to differentiate into dorsal foregut cells.

The first pancreatic induction medium is a chemically defined medium (CDM) which comprises an activin/TGFβ antagonist; FGF; retinoic acid; and a BMP antagonist. In some embodiments, these may be the only differentiation factors in the medium.

For example, the first pancreatic induction medium may consist of a chemically defined basal medium, such as advanced DMEM, supplemented with an activin/TGFβ antagonist, preferably SB-431542 (for example, 5 to 25 µM, preferably about 10 µM), FGF, preferably FGF10 (for example 5 to 100 ng/ml, preferably about 50 ng/ml), retinoic acid (for example at 0.5 to 20 µM, preferably about 2 µM) and a BMP antagonist, preferably noggin (for example 100 to 500 ng/ml).

Preferably, the population of definitive endoderm cells may be cultured for 2 to 4 days, most preferably 3 days to produce the population of dorsal foregut cells.

A population of dorsal foregut cells may express the markers; Hex, RFX6, FOXA2, HNF1b, SOX2, HNF4a, and HLXB9. Dorsal foregut cells may lack expression of markers associated with less differentiated cells, such as SOX17, CXCR4 and GSC.

Second and third pancreatic induction medium are employed to induce the dorsal foregut cells to differentiate into pancreatic progenitor cells.

The second pancreatic induction medium is a chemically defined medium (CDM) which comprises FGF, a BMP inhibitor, retinoic acid, and a hedgehog signalling inhibitor. In some embodiments, these may be the only differentiation factors in the medium.

For example, the second pancreatic induction medium may consist of a chemically defined basal medium, such as advanced DMEM, supplemented with an FGF, preferably FGF10 (for example at 5 to 100 ng/ml, preferably about 50 ng/ml); retinoic acid, (for example at 0.5 to 20 µM, preferably about 2 µM); hedgehog signalling inhibitor, preferably KAAD-cyclopamine (for example 0.1 to 1 µM, preferably 0.25 µM); and a BMP antagonist, preferably noggin (for example 5 to 500 ng/ml or 100 to 500 ng/ml, preferably about 50 ng/ml).

The dorsal foregut cells may be cultured in the second pancreatic induction medium for 2 to 4 days, most preferably 3 days.

Following culturing in the second pancreatic induction medium, the differentiating cells may be cultured in a third pancreatic induction medium.

The third pancreatic induction medium is a chemically defined medium (CDM) which comprises FGF. In some embodiments, FGF and optionally retinoic acid, may be the only differentiation factor(s) in the medium.

For example, the third pancreatic induction medium may consist of a chemically defined basal medium, such as advanced DMEM, supplemented with an FGF, preferably FGF10 or FGF7 (KGF) (for example at 5 to 100 ng/ml, preferably about 50 ng/ml). In some preferred embodiments, the chemically defined basal medium may be further supplemented with retinoic acid.

The cells may be cultured in the third pancreatic induction medium for 2 to 4 days, most preferably 3 days to produce a population of pancreatic progenitor cells.

A population of pancreatic progenitor cells may express the markers PDX1, SOX9, HNF6, NKX6.1 and PTF1a. Pancreatic progenitor cells may lack expression of markers associated with less differentiated cells, such as HLXB9.

In some embodiments, the pancreatic progenitor cells may be further differentiated and/or matured to produce a population of pancreatic endocrine cells. Suitable protocols for the maturation of pancreatic endocrine cells are available the art (see Kroon E et al. (2008) Nat Biotechnol 26: 443-452). For example, the pancreatic progenitor cells may be cultured in a first endocrine induction and a second endocrine induction The first endocrine induction medium is a chemically defined medium (CDM) which comprises a Notch signalling inhibitor. In some embodiments, the first endocrine induction medium may further comprise retinoic acid. In some embodiments, the Notch signalling inhibitor, and optionally retinoic acid, may be the only differentiation factor(s) in the medium. In addition to the Notch signalling inhibitor and optionally retinoic acid, the first endocrine induction medium may comprise a basal medium, preferably advanced DMEM, supplemented with a serum-free media supplement, preferably B27.

For example, the first endocrine induction medium may consist of a chemically defined basal medium, such as advanced DMEM, supplemented with B27 and Notch signalling inhibitor, preferably DAPT (for example at 0.1 to 10 mM, preferably about 1 mM). In some embodiments, the first endocrine induction medium may further comprise retinoic acid.

Suitable serum-free media supplements include B27 (Brewer et al Brain Res (1989) 494 65-74; Brewer et al J. Neurosci Res 35 567-576 (1993); Brewer et al Focus 16 1 6-9; Brewer et al (1995) J. Neurosci. Res. 42:674-683; Roth et al J Trace Elem Med Biol (2010) 24 130-137) and NS21 (Chen et al J. Neurosci Meths (2008) 171 239-247). Serum-free media supplements, such as B27 and N21, are well known in the art and widely available commercially (e.g. Invitrogen; Sigma Aldrich Inc).

The pancreatic progenitor cells may be cultured in the first endocrine induction medium for 2 to 4 days, most preferably 3 days.

The second endocrine induction medium may be a chemically defined medium (CDM) without additional differentiation factors or may comprise retinoic acid. The second endocrine induction medium may comprise a basal medium, preferably advanced DMEM, supplemented with a serum-free media supplement, preferably B27. In some embodiments, the second endocrine induction medium may further comprise retinoic acid.

The pancreatic progenitor cells may be cultured in the second endocrine induction medium for 2 to 4 days, most preferably 3 days.

A population of pancreatic endocrine cells may express the markers NGN3, INS, SST and GLU.

Preferably, the population of pancreatic endocrine cells may secrete insulin upon glucose stimulation.

Pancreatic endocrine cells may lack expression of markers characteristic of less differentiated pancreatic or endodermal cells, such as PDX1, SOX9, HNF6, NKX6.1 and PTF1a.

The culture of mammalian cells is well-known in the art (see, for example, Basic Cell Culture Protocols, C. Helgason, Humana Press Inc. U.S. (15 Oct. 2004) ISBN: 1588295451; Human Cell Culture Protocols (Methods in Molecular Medicine S.) Humana Press Inc., U.S. (9 Dec. 2004) ISBN: 1588292223; Culture of Animal Cells: A Manual of Basic Technique, R. Freshney, John Wiley & Sons Inc (2 Aug. 2005) ISBN: 0471453293, Ho W Y et al J Immunol Methods. (2006) 310:40-52, Handbook of Stem Cells (ed. R. Lanza) ISBN: 0124366430). Media and ingredients thereof may be obtained from commercial sources (e.g. Gibco, Roche, Sigma, Europa bioproducts, R&D Systems). Standard mammalian cell culture conditions may be employed for the above culture steps, for example 37° C., 21% Oxygen, 5%, Carbon Dioxide. Media is preferably changed every two days and cells allowed to settle by gravity.

The population may contain 80% or more, 85% or more, 90% or more, or 95% or more pancreatic progenitor cells or, if matured, pancreatic endocrine cells, following culture in the medium.

In some embodiments, the population of pancreatic progenitor cells or pancreatic endocrine cells may be substantially free from other cell types, such that that no further purification is required. For example, the population may be homogenous or substantially homogeneous.

Pancreatic progenitor cells or pancreatic endocrines produced at any stage in the methods described herein may be isolated and/or purified.

Pancreatic progenitor cells or endocrine cells may be separated from other cell types in the population using any technique known to those skilled in the art, including those based on the recognition of extracellular epitopes by antibodies and magnetic beads or fluorescence activated cell sorting (MACS or FACS) including the use of antibodies against extracellular regions of characteristic markers as described above.

Populations of pancreatic progenitor cells or pancreatic endocrine cells produced as described herein may be expanded, propagated or maintained using standard mammalian cell culture techniques.

In some embodiments, populations of pancreatic progenitor cells or pancreatic endocrine cells may be grown or maintained in three-dimensional (3D) culture systems. Suitable 3D systems, for example scaffolds of synthetic or natural polymers, are known in the art and available from commercial suppliers (e.g. Sigma-Aldrich).

The ability of the pancreatic progenitor or endocrine cells in the population to perform one or more pancreatic cell functions may be monitored and/or determined. For example, the ability of the cells to perform one or more of; insulin expression, insulin secretion, glucose responsive and engraftment into animal models may be monitored and/or determined.

Suitable methods for determining pancreatic cell function are well known in the art.

In some embodiments, the populations of pancreatic progenitor cells or pancreatic endocrine cells produced as described herein may be stored, for example by lyophilisation and/or cryopreservation. Another aspect of the invention provides a population of isolated pancreatic progenitor cells or pancreatic endocrine cells produced by a method described above.

The population may contain 80% or more, 85% or more, 90% or more, or 95% or more or pancreatic progenitor or pancreatic endocrine cells.

The cells may be clinical grade cells which have not been exposed to undefined media components or other potential contaminants.

The cells may display one or more functions or functional characteristics of mature pancreatic cells or may be capable of displaying one or more such functions or functional characteristics following engraftment or transplantation into a mammalian host. For example, the cells may be capable of one or more of insulin expression; insulin secretion; and glucose responsiveness, either without engraftment or following engraftment into a mammalian host. A population of pancreatic progenitor cells or pancreatic endocrine cells may be used in a method of treatment, for example the treatment of a patient with a pancreatic condition, such as diabetes. A population may also be used in the manufacture of a medicament for use in the treatment of a pancreatic condition, such as diabetes.

In some embodiments, pancreatic progenitor cells or pancreatic endocrine cells which are administered to an individual may be genetically manipulated to produce a therapeutic molecule, for example a drug or growth factor (Behrstock S et al, Gene Ther 2006 March; 13(5):379-88, Klein S M et al, Hum Gene Ther 2005 April; 16(4):509-21).

Other aspects of the invention relate to methods of using the populations of isolated pancreatic progenitor cells or pancreatic endocrine cells in therapy or in the production of mature pancreatic cells for use in therapy.

A method of treating a pancreatic condition may comprise;
  administering a population of isolated pancreatic progenitor cells or pancreatic endocrine cells produced as described herein an individual in need thereof.

Pancreatic conditions suitable for treatment may include hereditary and familial pancreatitis and diabetic conditions, such as type I and type II diabetes.

The pancreatic progenitor cells or pancreatic endocrine cells may be transplanted, infused or otherwise administered into the pancreas of the individual. Suitable techniques are well known in the art.

Cells for use in methods of treatment may be formulated into therapeutic compositions.

Aspects of the invention extend to a therapeutic composition, medicament, or other composition comprising pancreatic progenitor cells or pancreatic endocrine cells produced as described herein, a method comprising administration of such pancreatic progenitor cells or pancreatic endocrine cells to a patient, e.g. for treatment (which may include preventative treatment) of a pancreatic condition, as described above, and a method of making a therapeutic composition comprising admixing such pancreatic progenitor cells or pancreatic endocrine cells or pancreatic endocrine cells with a therapeutically acceptable excipient, vehicle or carrier, and optionally one or more other ingredients.

A therapeutic composition according to the present invention, and for use in accordance with the present invention, may comprise, in addition to the cells, a pharmaceutically acceptable excipient, carrier, buffer, preservative, stabiliser, anti-oxidant or other material well known to those skilled in the art. Such materials should be non-toxic and should not interfere with the activity of the cells. The precise nature of the carrier or other material will depend on the route of administration.

Liquid therapeutic compositions generally include a liquid carrier such as water, petroleum, animal or vegetable oils, mineral oil or synthetic oil. Physiological saline solution, tissue or cell culture media, dextrose or other saccharide solution or glycols such as ethylene glycol, propylene glycol or polyethylene glycol may be included.

The composition may be in the form of a parenterally acceptable aqueous solution, which is pyrogen-free and has suitable pH, isotonicity and stability. Those of relevant skill in the art are well able to prepare suitable solutions using, for example, isotonic vehicles such as Sodium Chloride, Ringer's Injection, or Lactated Ringer's Injection. A composition may be prepared using artificial cerebrospinal fluid.

Pancreatic progenitor cells or pancreatic endocrine cells may be implanted or infused into a patient by any technique known in the art (e.g. Lindvall, O. (1998) Mov. Disord. 13, Suppl. 1:83-7; Freed, C. R., et al., (1997) Cell Transplant, 6, 201-202; Kordower, et al., (1995) New England Journal of Medicine, 332, 1118-1124; Freed, C. R., (1992) New England Journal of Medicine, 327, 1549-1555, Le Blanc et al, Lancet 2004 May 1; 363(9419):1439-41). In particular cell suspensions may be injected or infused into the pancreas of a patient or into an adjacent region or injected into the portal vein of a patient. Pancreatic progenitor cells or pancreatic endocrine cells may be injected alone or in combination with other cells such as endothelial cells. In some embodiments, cells may be used to form vascularised tissues ex-vivo before implantation.

Administration of a composition in accordance with the present invention is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors.

A composition may be administered alone or in combination with other treatments, either simultaneously or sequentially dependent upon the condition to be treated.

In some preferred embodiments, pancreatic progenitor and endocrine cells produced as described herein may be useful in the treatment of diabetic conditions, such as type I and II diabetes.

Other aspects of the invention relate to methods of using the populations of isolated pancreatic progenitor cells or pancreatic endocrine cells in disease modelling and/or screening.

For example, isolated populations of pancreatic progenitor cells or pancreatic endocrine cells may be useful in modelling pancreatic conditions. Pancreatic conditions may include genetic disorders affecting pancreas development and non-genetic conditions, including diabetic conditions such as type 1 and type 2 diabetes.

As described above, pancreatic progenitor cells or pancreatic endocrine cells may be generated from iPS cells from an individual with a genetic disorder, preferably a monogenetic disorder. Pancreatic progenitor cells or pancreatic endocrine cells with the genotype of a genetic disorder may be useful in modelling or characterising pancreatic conditions and their effects. A pancreatic progenitor cell or pancreatic endocrine cell with the genotype of a genetic disorder may display a phenotype associated with the pancreatic condition or one or more pathologies associated with the pancreatic condition. This may be useful in disease modelling and screening for therapeutic compounds.

Genetic disorders include diseases associated with pancreatic dysfunction or development, such as pancreatic agenesis, hereditary and familial pancreatitis, Schwachman-Diamond syndrome, type 1 and type-2 diabetes and pancreatic cancer.

A method of producing a population of pancreatic progenitor cells or pancreatic endocrine cells with a genetic disorder genotype may comprise;
  providing iPS cells from an individual with a genetic disorder, and;
  producing a population of pancreatic progenitor cells or pancreatic endocrine cells from the iPS cells as described above,
  said pancreatic progenitor cells or pancreatic endocrine cells having the genetic disorder genotype.

Once produced, a population of pancreatic progenitor cells or pancreatic endocrine cells with the genetic disorder genotype may be cultured, expanded and maintained, for example for use in disease modelling or screening.

A method of screening a compound may comprise;
  contacting isolated pancreatic progenitor cells or pancreatic endocrine cells produced by a method described herein with a test compound, and;
  determining the effect of the test compound on said pancreatic progenitor cells or pancreatic endocrine cells and/or the effect of said cells on the test compound.

The proliferation, growth or viability of pancreatic progenitor cells or pancreatic endocrine cells or their ability to perform one or more cell functions may be determined in the presence relative to the absence of the test compound. A decrease in proliferation, growth, viability or ability to perform one or more cell functions is indicative that the compound has a toxic effect and an increase in growth, viability or ability to perform one or more cell functions is indicative that the compound has an ameliorative effect Cell functions may include insulin expression, insulin secretion or glucose responsiveness of the pancreatic progenitor cells or pancreatic endocrine cells.

For example, the ability of a test compound to increase insulin secretion and/or stimulate proliferation of pancreatic progenitor cells or pancreatic endocrine cells as described herein may be determined.

Gene expression in the cells may be determined in the presence relative to the absence of the test compound. For example, the expression of a pancreatic marker such as NGN3, INS, SST, GLU, PDX1, SOX9, HNF6, NKX6.1 and PTF1a, may be determined. A decrease in expression is indicative that the compound has a cytotoxic effect.

Gene expression may be determined at the nucleic acid level, for example by RT-PCR, or at the protein level, for example, by immunological techniques, such as ELISA, or by activity assays.

In some embodiments, phenotypic state of the pancreatic progenitor cells or pancreatic endocrine cells may be determined by high-content screening. Suitable techniques and apparatus for high content screening are well known in the art and include confocal imaging platforms, such as ImageXpress Ultra™ (Molecular Devices USA), Opera™ (PerkinElmer Inc MA USA, and IN Cell 3000™ (GE Amersham Biosciences, UK), and widefield imaging platforms, such as Arrayscan VTI™, (Cellomics) and IN Cell Analyzer 2000™ (GE Healthcare NJ USA).

Pancreatic progenitor cells or pancreatic endocrine cells used in screening or modelling methods may display a normal genotype or a genetic disorder genotype.

Methods as described herein may be useful in identifying compounds with activity useful in the treatment of a pancreatic condition or in the development of therapeutic compounds for such treatment. For example, a method may comprise the step of identifying a test compound which reduces or ameliorates one or more pancreatic phenotypes or symptoms of a disease condition or pancreatic disorder in the pancreatic progenitor cells or pancreatic endocrine cells. Compounds which reduce disease symptoms or phenotypes may be useful in the development of therapeutics for the treatment of the pancreatic condition or its symptoms.

A test compound identified using one or more initial screens as having a beneficial effect on the pancreatic progenitor cells or pancreatic endocrine cells may be assessed further using one or more secondary screens.

A secondary screen may involve testing for a biological function or activity in vitro and/or in vivo, e.g. in an animal model. For example, the ability of a test compound to reduce or ameliorate the progression of the disorder or one or more symptoms or pathologies associated with the pancreatic disorder in an animal model of the disease may be determined.

Following identification of a test compound which reduces or ameliorates one or more symptoms of a pancreatic disorder in the pancreatic progenitor cells or pancreatic endocrine cells, and/or stimulates insulin secretion and/or proliferation, the compound may be isolated and/or purified or alternatively it may be synthesised using conventional techniques of recombinant expression or chemical synthesis. Furthermore, it may be manufactured and/or used in preparation, i.e. manufacture or formulation, of a composition such as a medicament, therapeutic composition or drug. These may be administered to individuals for the treatment of the pancreatic condition or its symptoms.

In some preferred embodiments, pancreatic progenitor and endocrine cells produced as described herein may be useful in the modelling diabetic conditions, such as type I and II diabetes and identifying compounds which display activities which may be useful in the treatment of diabetic conditions.

Other aspects and embodiments of the invention provide the aspects and embodiments described above with the term "comprising" replaced by the term "consisting of" and the aspects and embodiments described above with the term "comprising" replaced by the term "consisting essentially of".

Modifications of the above embodiments, further embodiments and modifications thereof will be apparent to the skilled person on reading this disclosure, and as such these are within the scope of the present invention.

All documents and sequence database entries mentioned in this specification are incorporated herein by reference in their entirety for all purposes.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

It is to be understood that the application discloses all combinations of any of the above aspects and embodiments described above with each other, unless the context demands otherwise. Similarly, the application discloses all combinations of the preferred and/or optional features either singly or together with any of the other aspects, unless the context demands otherwise.

Certain aspects and embodiments of the invention will now be illustrated by way of example and with reference to the figures described below.

Figure 2:
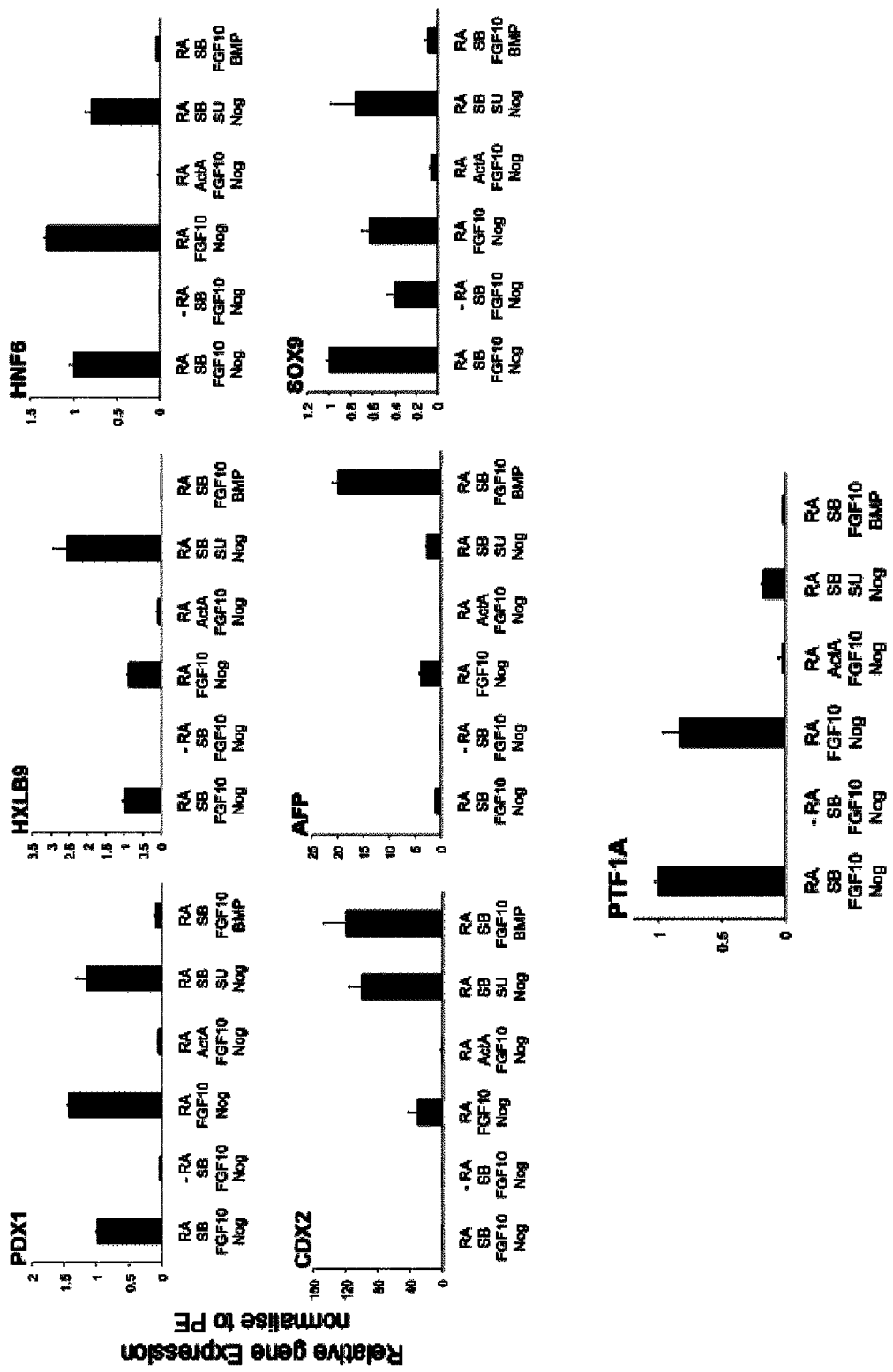
FIGS. 2 to 4 show the differentiation of hESCs derived definitive endoderm into pancreatic progenitor in defined culture conditions.

FIG. 2 shows the function of RA, BMP, FGF10 and Activin/TGF 0 on pancreatic differentiation of DE cells generated from hESCs. QPCR analyses showing the expression of PDX1/HLXB9/HNF6/CDX2/AFP/SOX9/PTF1A in DE cells grown for 3 days in the presence of diverse combination of Retinoic Acid (RA), SB431542 (SB) or Activin 10 ng/ml (Act), FGF10 50 ng/ml (FGF) or SU5402 10 μM (SU), and Noggin 100 ng/ml (Nog) or BMP4 10 ng/ml.

Figure 3:
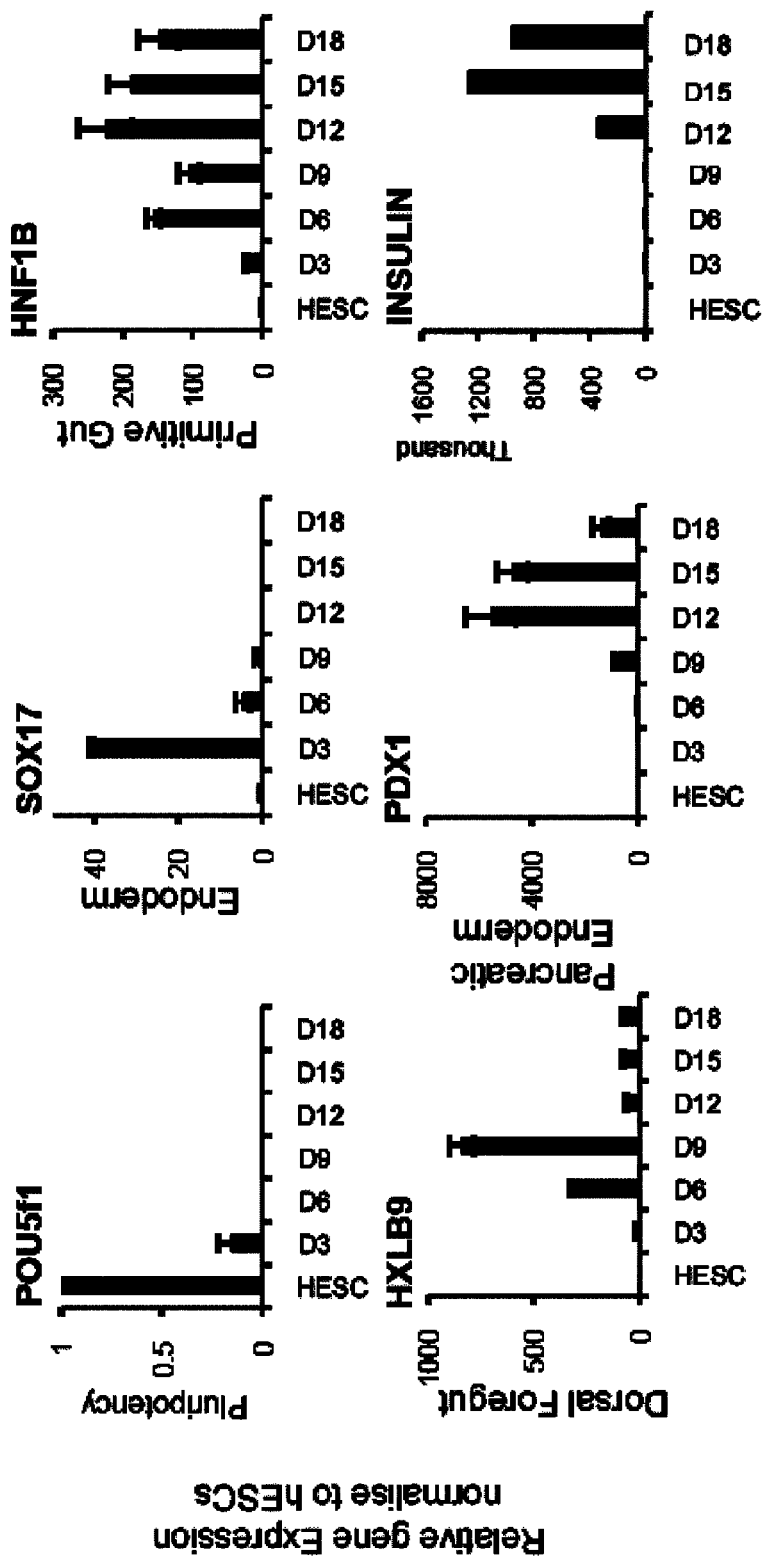

FIG. 3 shows the successive expression of markers showing patterning of definitive endoderm into foregut and then successive differentiation toward pancreatic progenitor and hormonal expressing cells.

Figure 4:
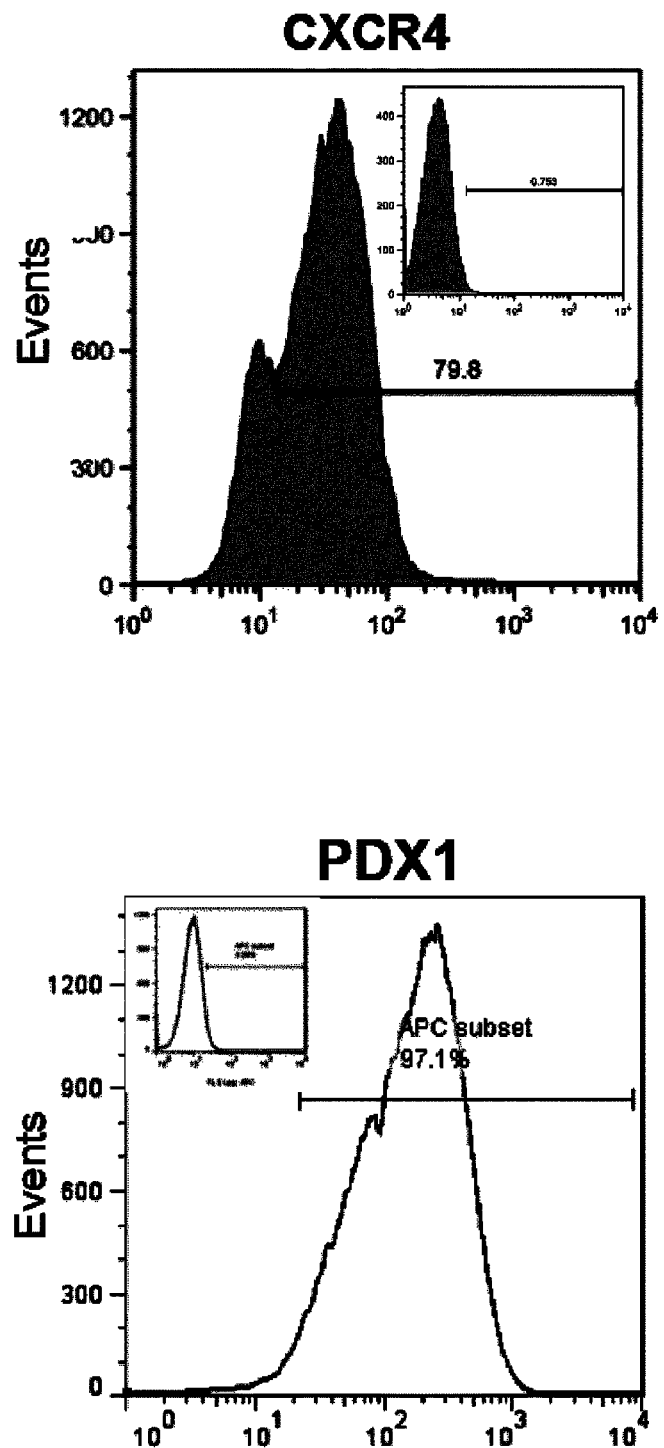

FIG. 4 shows FACS analyses showing expression of CXCR4 in DE cells (Day 3) and PDX1 in pancreatic progenitor (Day 12). Conjugated Isotype controls were used as negative control to gate positive population.

Figure 5:
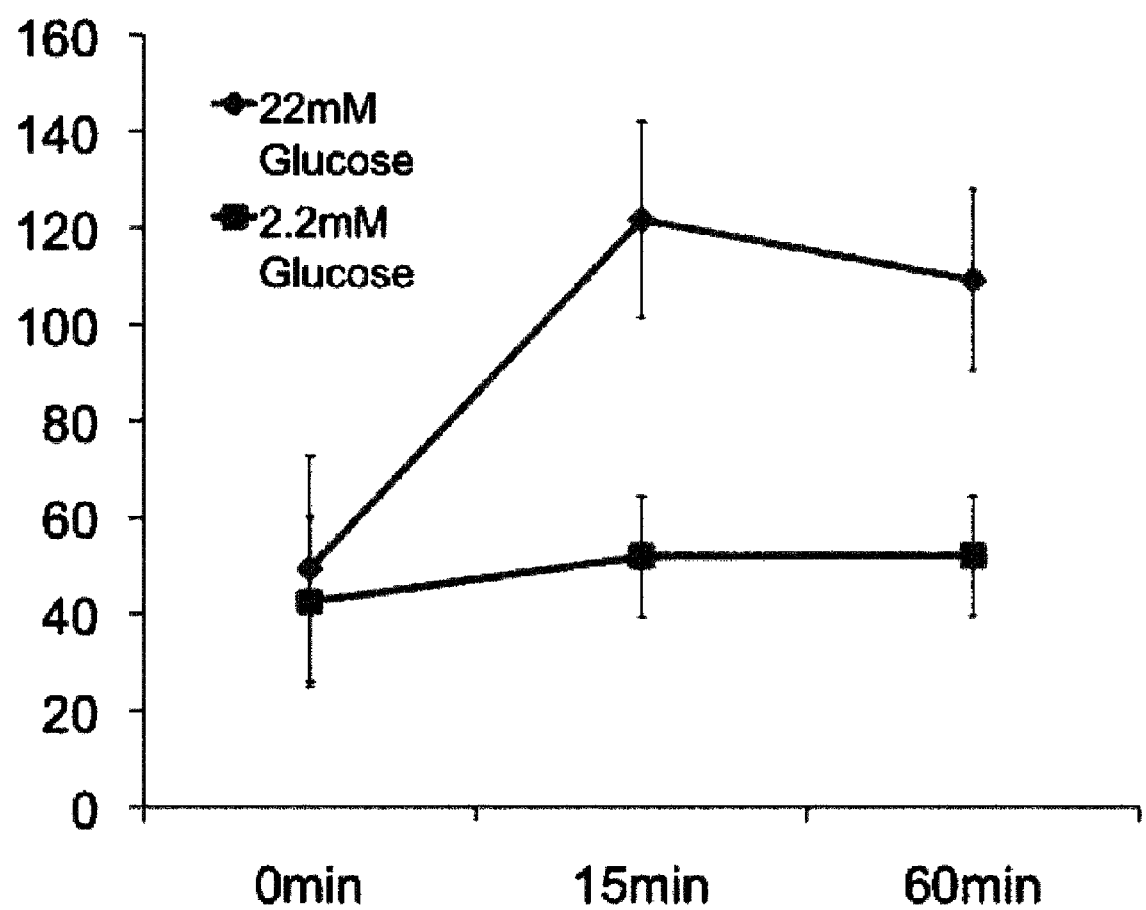
Figure 6:
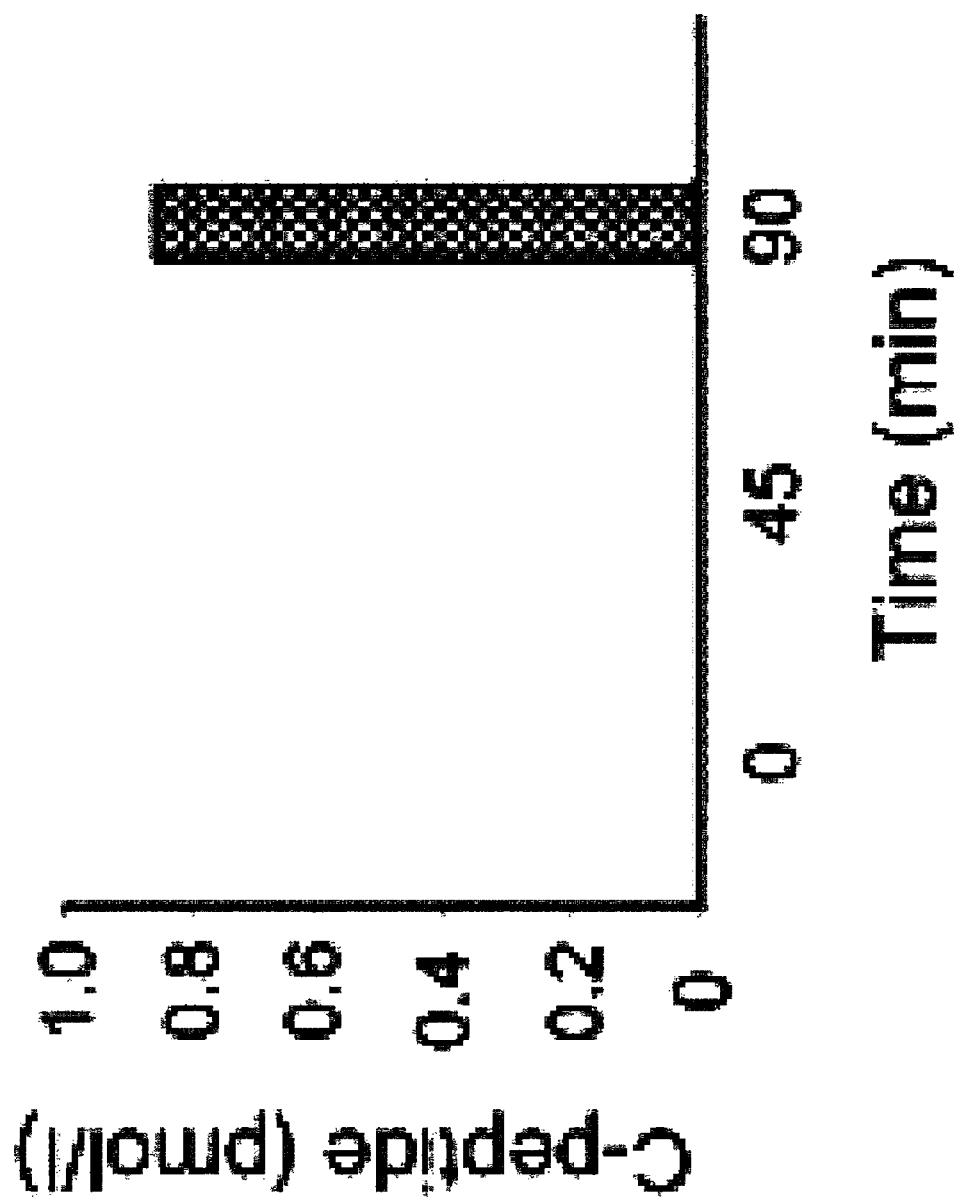

FIGS. 5 and 6 shows pancreatic progenitors generated from dorsal foregut can differentiate into hormone expressing cells in vitro and in vivo.

FIG. 5 shows C-peptide secretion upon glucose stimulation in culture medium of endocrine cells generated from pancreatic progenitor (Day 18). Data are presented as average of 3 biological replicates and error bars indicate standard deviation. Cells grown in low glucose (2.2 mM) were used as negative control.

FIG. 6 shows mice transplanted with pancreatic progenitors (Day 12) were injected intraperitonealy with glucose 20 weeks after transplantation. Blood samples were taken at indicated time for C peptide measurement using ELISA. ND=Not Detected, Broken line=Assay limit.

Figure 7:
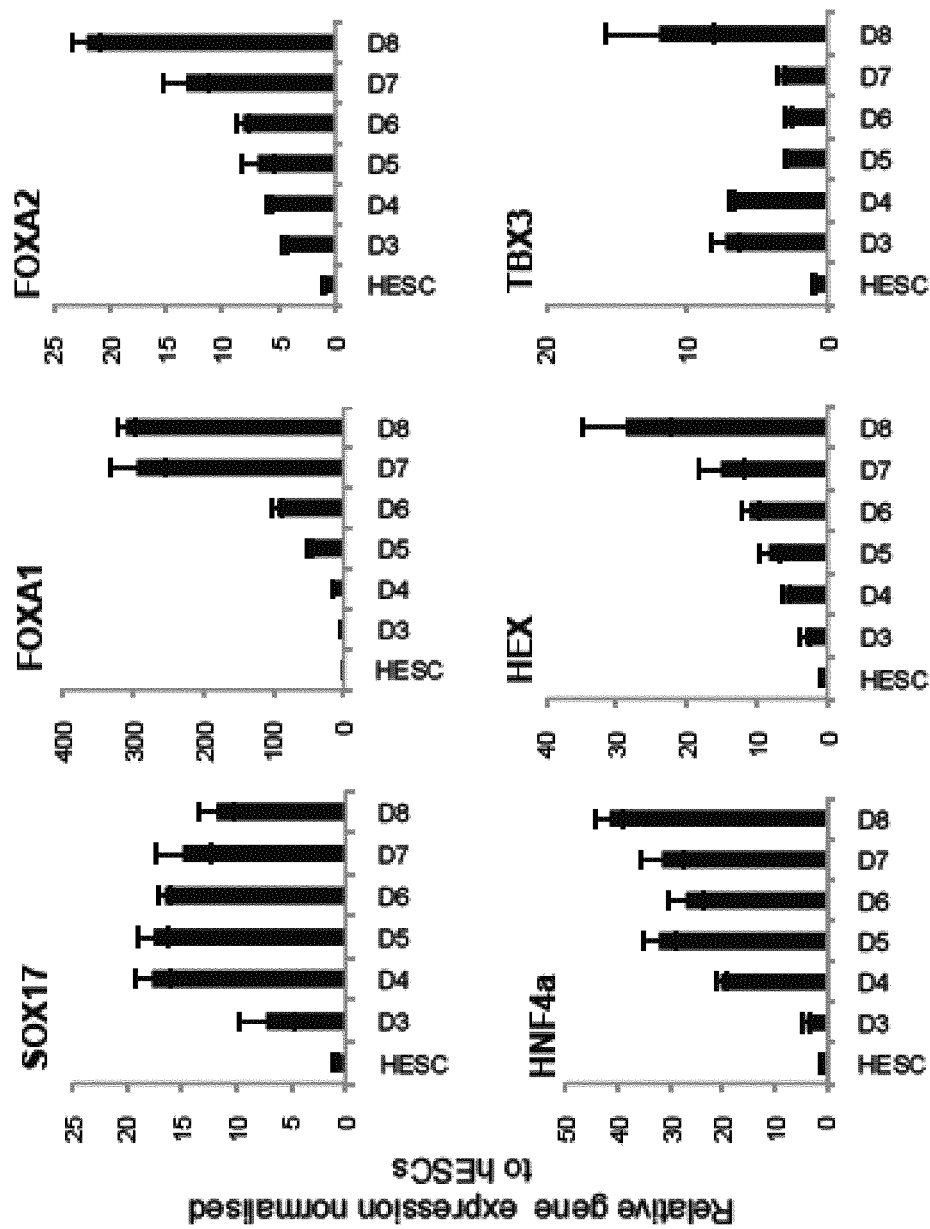
Figure 8:
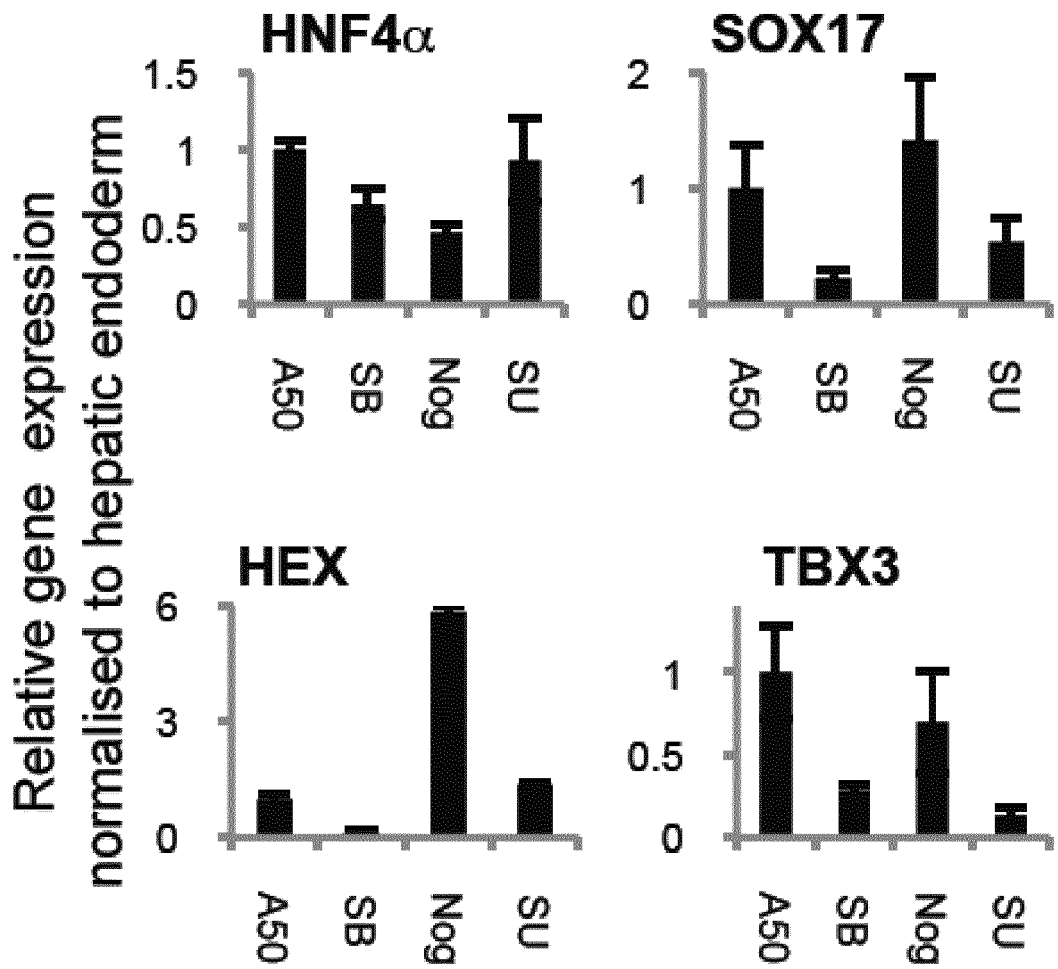

FIGS. 7 and 8 shows that activin induces specification of definitive endoderm into ventral foregut.

FIG. 7 shows expression of VF and liver bud markers in DE cells grown for 5 days in the presence of Activin.

FIG. 8 shows Q-CPR analyses showing that inhibition of Activin signalling by SB431542 (SB), BMP by Noggin (Nog) and FGF by SU5402 decreases the expression of hepatic markers in DE cells.

FIGS. 9 to 12 show differentiation of hESCs derived definitive endoderm into foetal hepatocytes in defined culture conditions.

Figure 9:
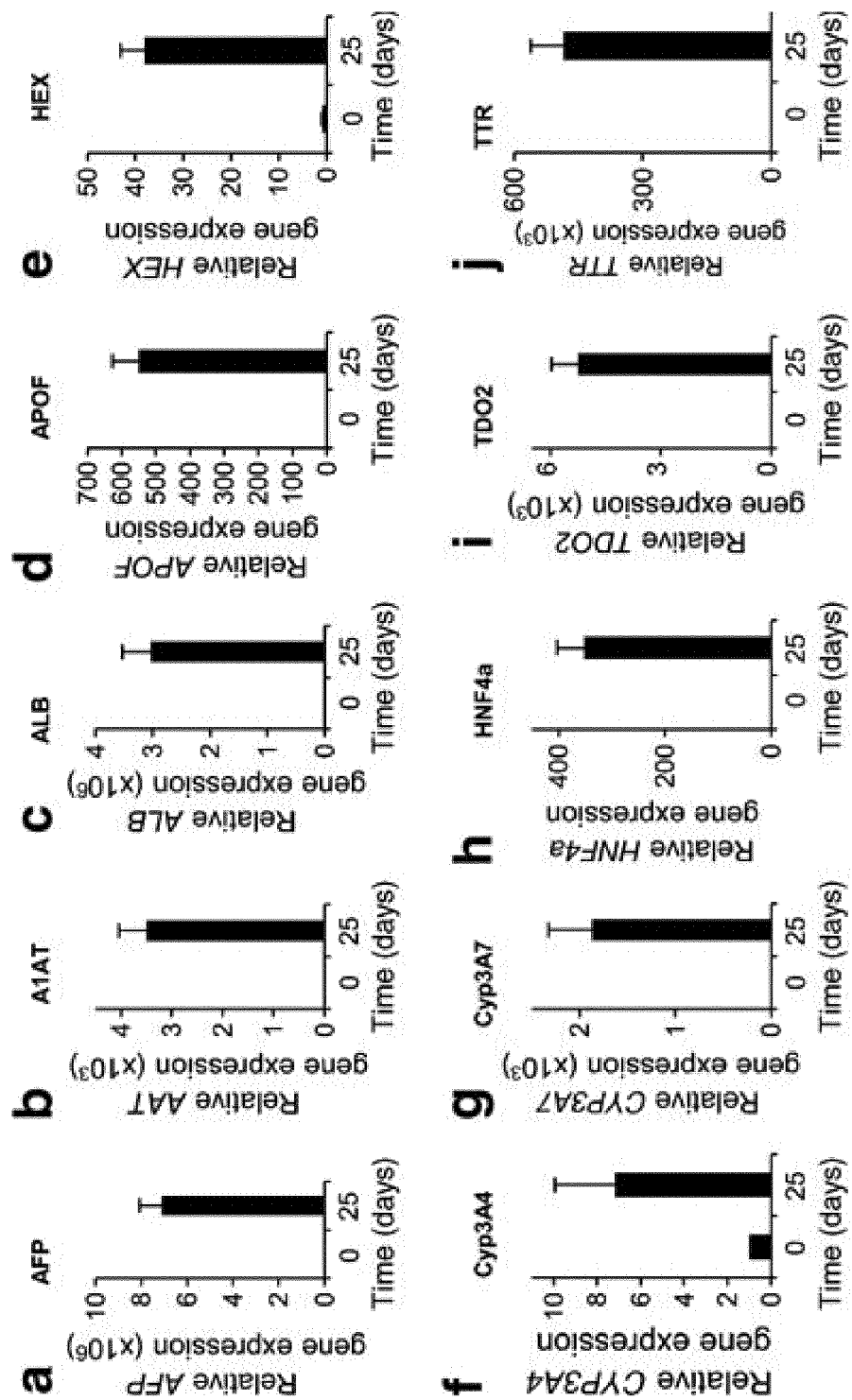

FIG. 9 shows expression of hepatocyte markers in DE cells grown for 25 days in conditions inductive for hepatic differentiation.

Figure 10:
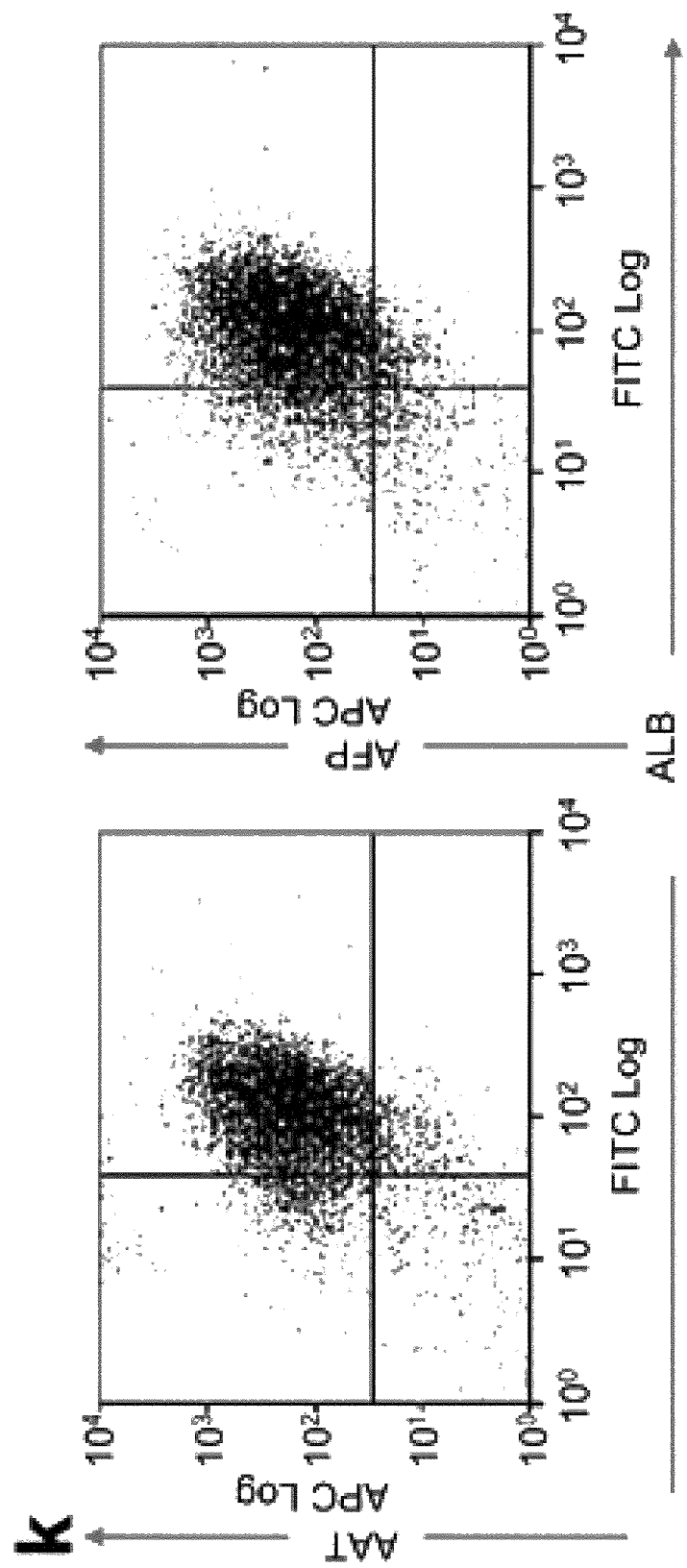

FIG. 10 shows FACS analyses showing the co-expression of Albumin (ALB) α-1-antitrypsin (AAT) and α-1-Fetoprotein (AFP) in hESCs derived foetal hepatocytes (Day 25).

Figure 11:
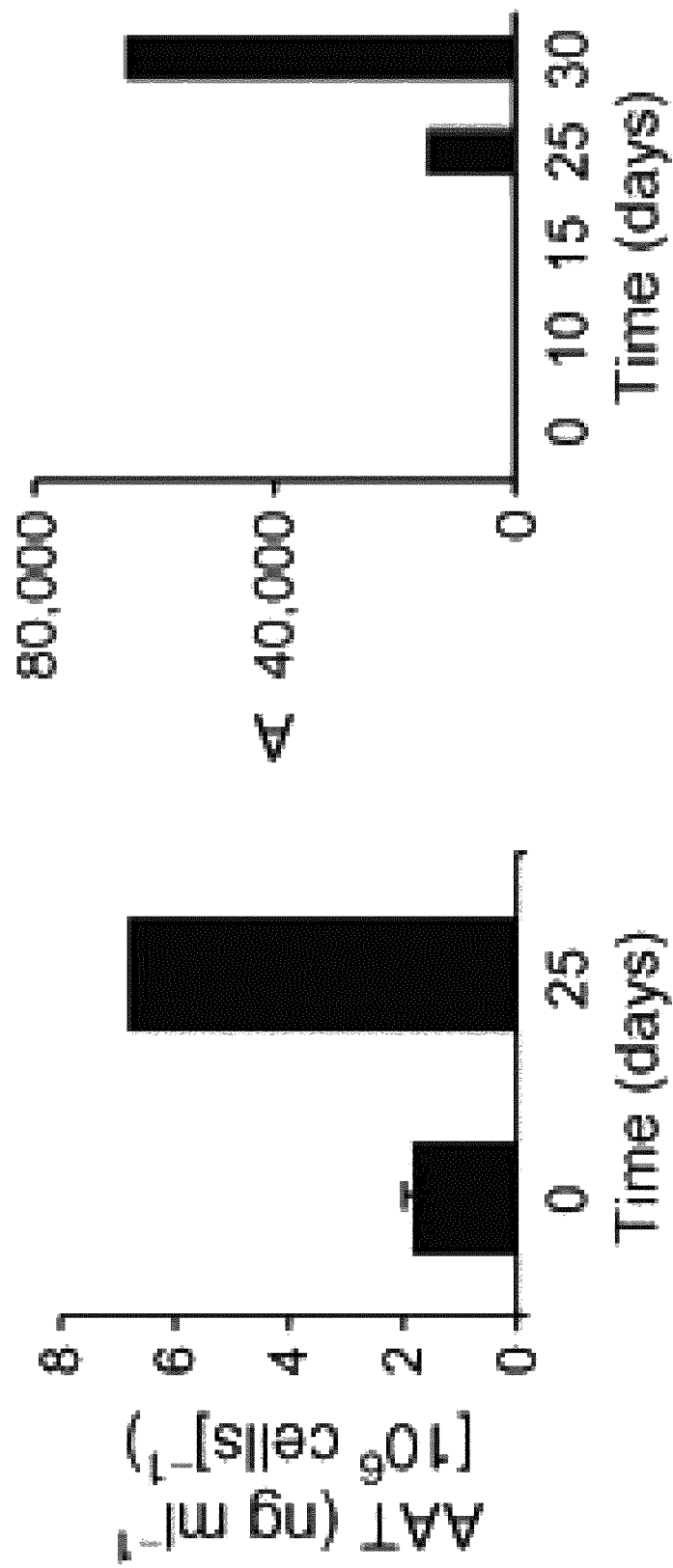

FIG. 11 shows ELISA analyses showing Alpha1-antytripsin (AAT) and Albumin secretion in culture media of hESCs derived foetal hepatocytes.

Figure 12:
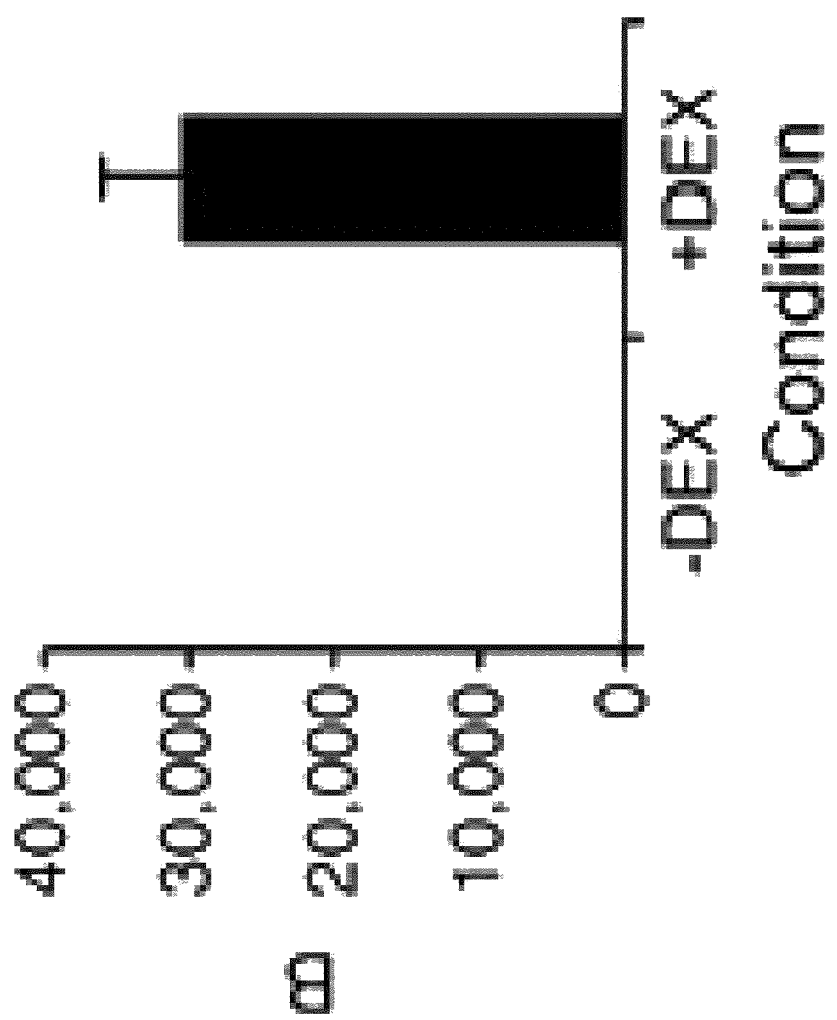

FIG. 12 shows inducible activity of CYP3A4 by dexamethasone (DEX) in hESCs derived foetal hepatocytes.

FIGS. 13 to 16 show that HEX is necessary for hepatic specification of ventral foregut in vitro.

Figure 13:
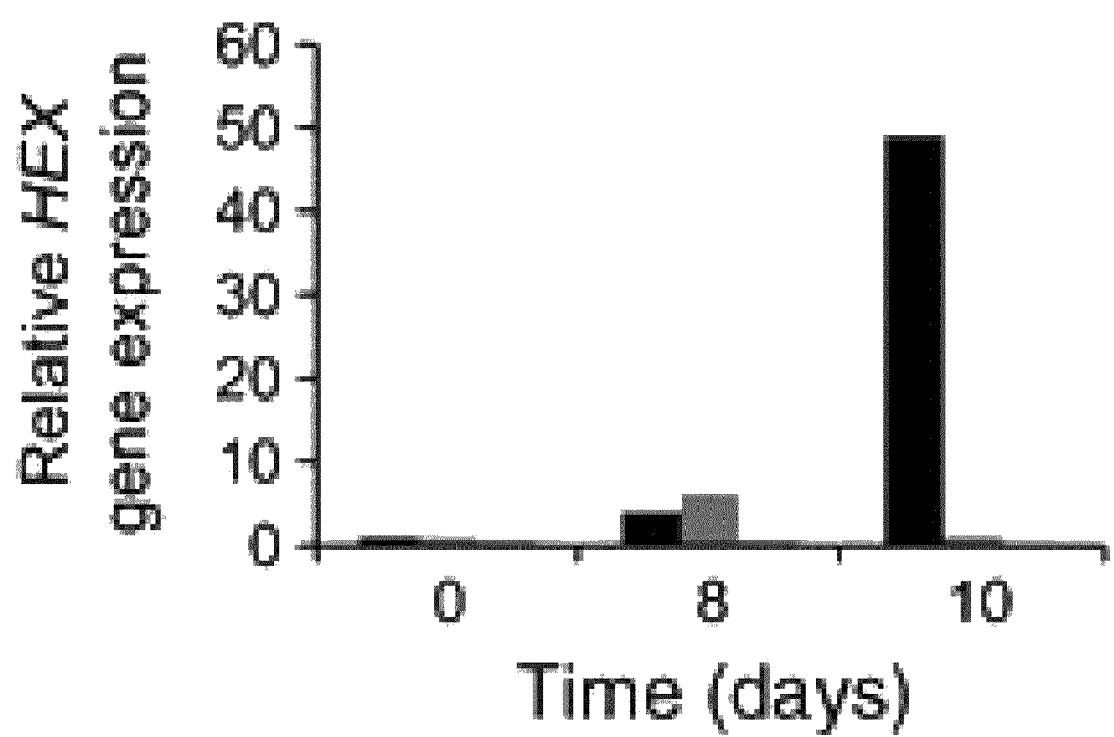

FIG. 13 shows Q-PCR analyses showing knock down of HEX in ShHEX-hESCs (shHEX98 and shHEX02) differentiating into hepatic endoderm. ShScramble-hESCs were used as negative control.

Figure 14:
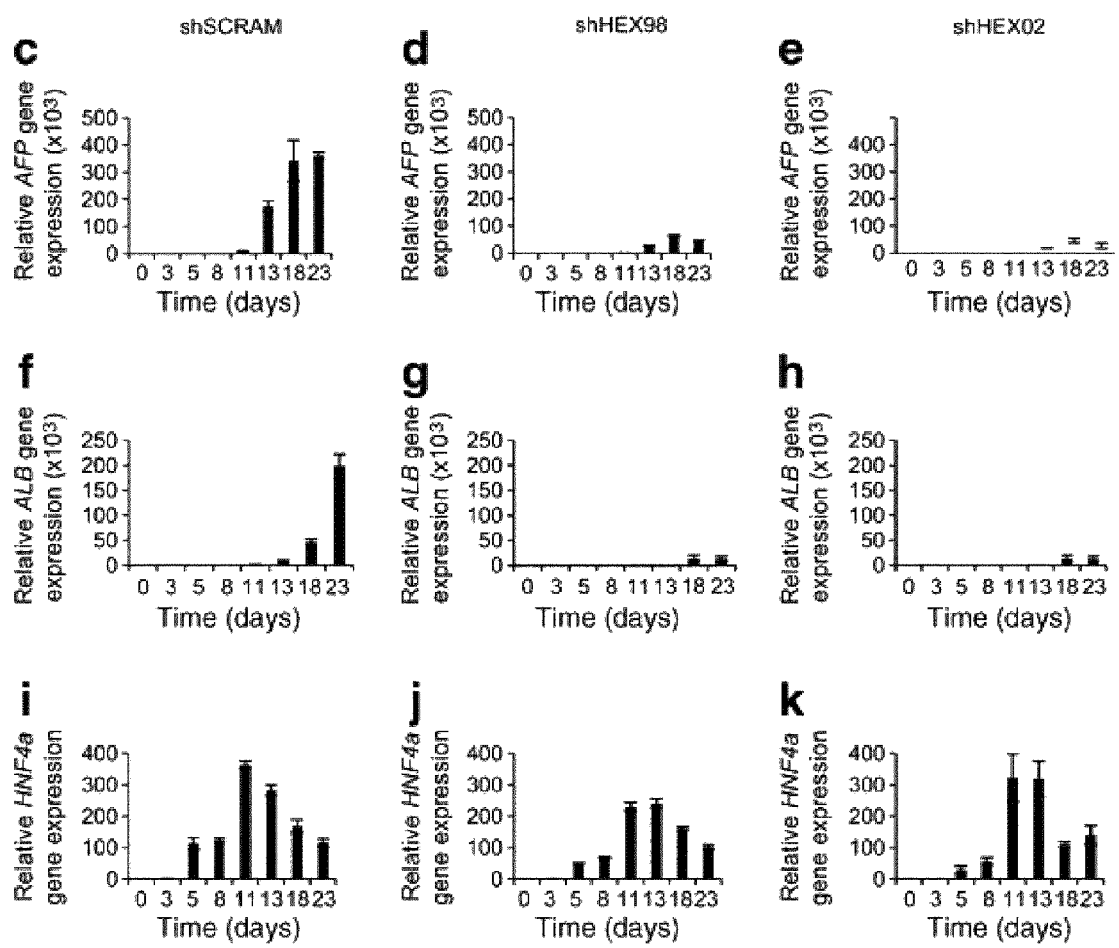

FIG. 14 shows Q-PCR analyses showing the effect of HEX knock down on hepatic specification of ventral foregut cells.

Figure 15:
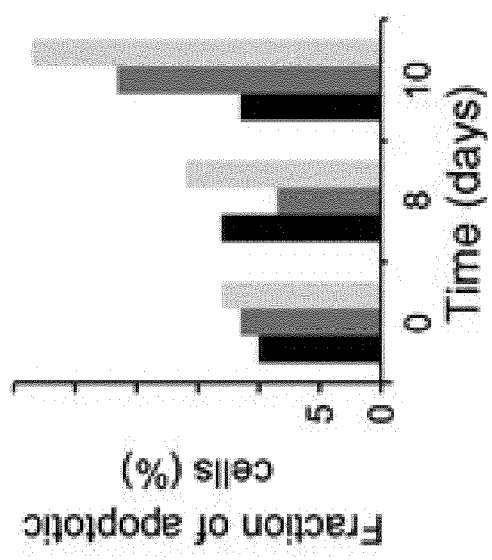

FIG. 15 shows a fraction of apoptotic cells in ShScramblehESCs and in ShHEX-hESCs differentiating into hepatic endoderm.

Figure 16:
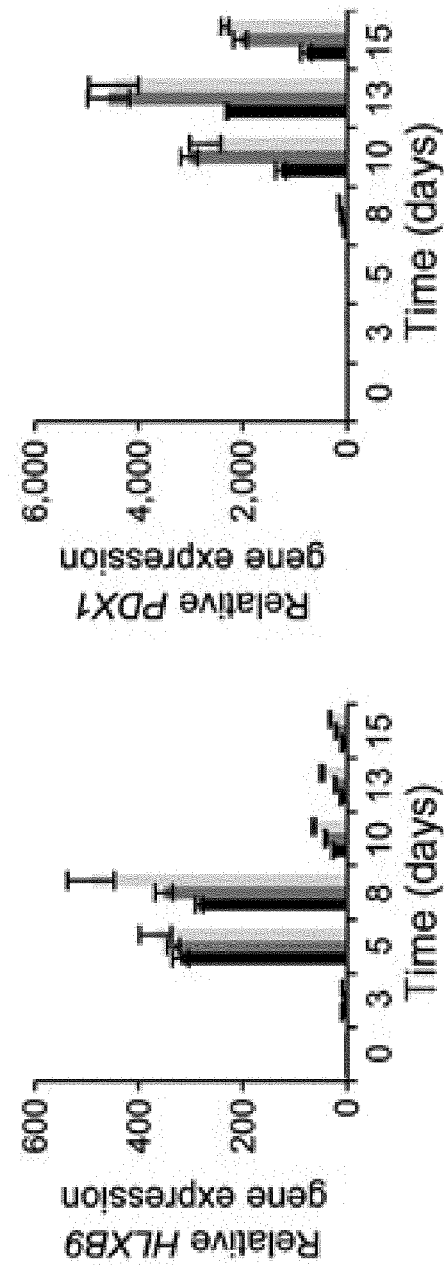

FIG. 16 shows expression of pancreatic markers in ShHEX-hESCs differentiating into pancreatic progenitor.

Figure 17:
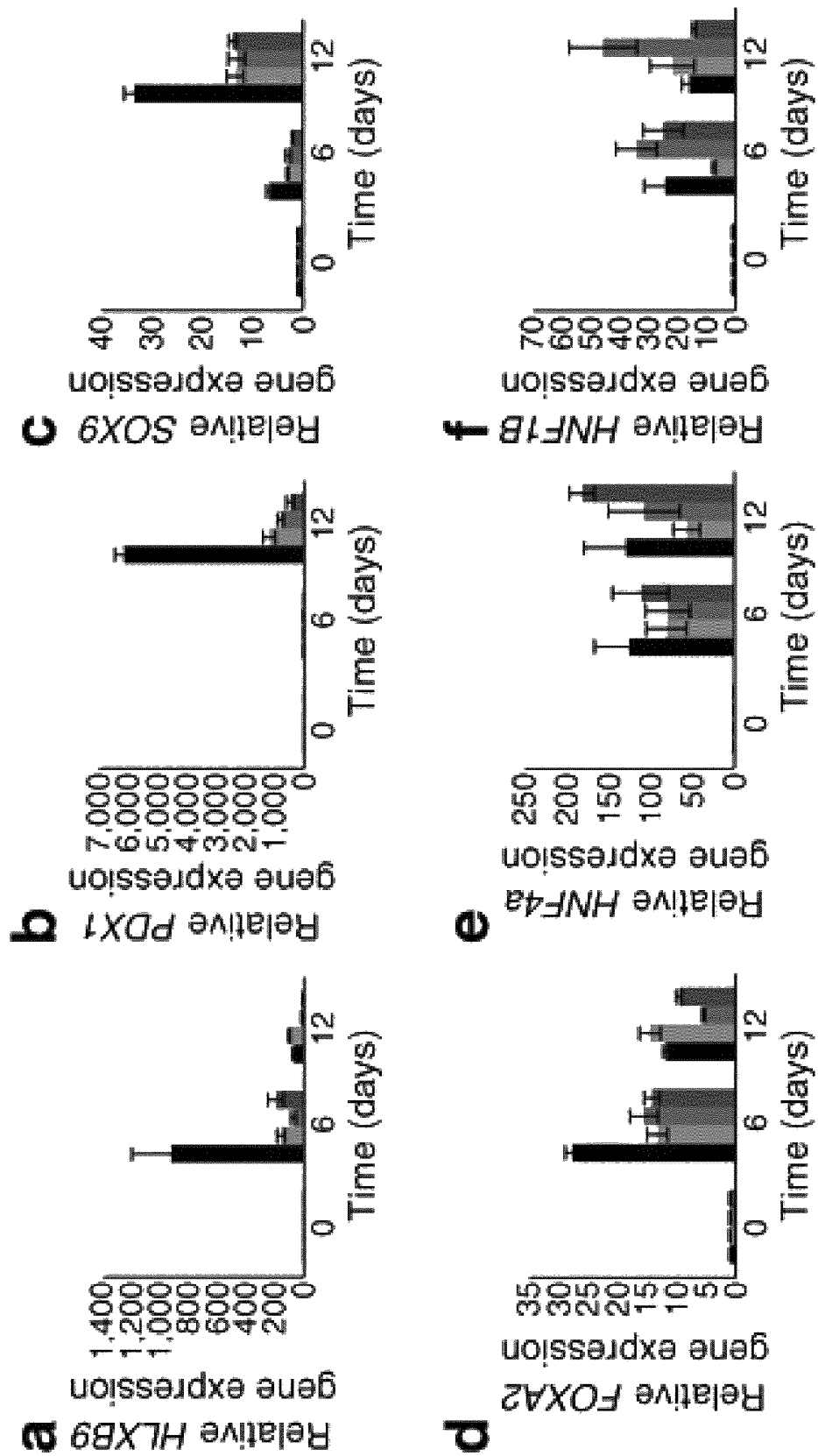
Figure 18:
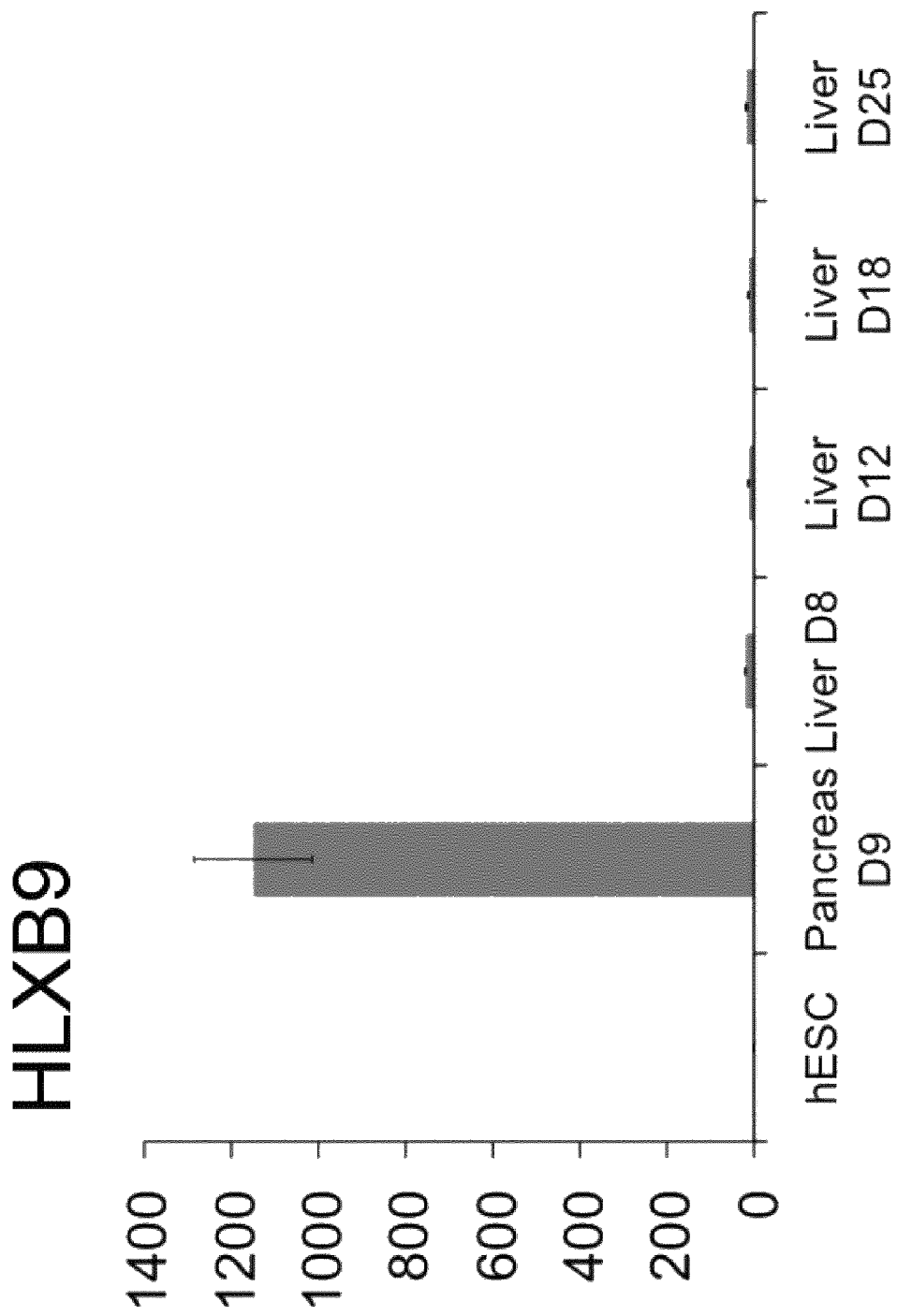

FIGS. 17 and 18 show that HLXB9 is necessary for pancreatic specification of dorsal foregut in vitro.

FIG. 17 shows Q-PCR analyses showing the effect of hHLXB9 knock down on pancreatic differentiation.

FIG. 18 shows expression of HLXB9 during hepatic differentiation. hESCs were grown for 25 days in culture inductive for hepatic differentiation and analysed for the expression of HXLB9 every 6 days (Day 12=D12, Day 18=D18, Day 25=D25) using Q-PCR. hESCs were used as negative control and pancreatic progenitors differentiated for 9 days (Pancreatic D9) were used as positive control.

EXPERIMENTS hESCs and hIPSCs Culture Conditions hESCs (H9 from WiCell) and hIPSCs (BBHX8, A1ATD-1, JRO1D) (Rashid S, et al. (2010) J Clin Invest 120: 3127-3136) were grown in defined culture (Brons et al (2007) Nature 448: 191-195). Cells were passaged weekly using collagenase IV and maintained in chemically defined medium (CDM) supplemented with Activin A (10 ng/ml) and FGF2 (12 ng/ml) as described previously ((Brons et al (2007)). Differentiation was carried out as described in FIG. 1. Daily media changes were made during the entire differentiation protocol. After the DE stage (stage 1), cells were cultured in Advanced DMEM (Invitrogen) supplemented with SB-431542 (10 µM; Tocris), FGF10 (50 ng/ml; AutogenBioclear), all-trans retinoic acid (RA, 2 µM; Sigma) and Noggin (50 ng/ml; R&D Systems) for 3 days. For stage 3, the cells were cultured in Advanced DMEM+human FGF10 (50 ng/ml; AutogenBioclear), all-trans retinoic acid (RA, 2 µM; Sigma), KAAD-cyclopamine (0.25 µM; Toronto Research Chemicals) and Noggin (50 ng/ml; R&D Systems) for 3 days. For Stage 4, the cells were cultured in human KGF (FGF7) or FGF10 (50 ng/ml; R&D Systems) for 3 days. For maturation of pancreatic progenitors, cells were grown in Advanced DMEM+1% vol/vol B27 and DAPT (1 mM) for 3 days and for 3 additional days in Advanced DMEM+1% vol/vol B27. Alternatively, for Stage 4, the cells were cultured in human KGF (FGF7) or FGF10 (50 ng/ml; R&D Systems) and all-trans retinoic acid (RA, 2 µM; Sigma) for 3 days. Alternatively for maturation of pancreatic progenitors, cells were grown in Advanced DMEM+1% vol/vol B27, all-trans retinoic acid (RA, 2 µM; Sigma) and DAPT (1 mM) for 3 days and for 3 additional days in Advanced DMEM+1% vol/vol B27 and all-trans retinoic acid (RA, 2 µM; Sigma).

RT-QPCR, Immunostaining, and FACS Analyses

Methods for RT-QPCR were described in Touboul T et al. (2010). Hepatology 51: 1754-1765. All data are presented as average of 3 independent biological triplicates and error bars indicate standard deviation.

Cytochrome P450 Activity

Cyp3A4 activity assay was measured in triplicate using the P450-Glo assay kit (Promega) according to the manufacturer's instructions. Cytochrome activity was then analysed using a P450-GloMax 96 microplate luminometer.

Periodic Acid Schiff (PAS) Staining

PAS staining was carried out on cells in triplicate using a kit (Sigma 395B-1KT) under the guidance of manufacturer's instructions. Diastase digestion was subsequently performed to confirm the positive staining was due to presence of Glycogen.

Uptake of LDL

The Dil-LDL staining kit was purchased from (Cayman Chemicals, MA) and the assay was performed according to the manufacturer's instructions.

HEX and HLXB9 Knockdown hESCs (H9) were stably transfected with expression vectors for ShRNA directed against HEX and HLXB9 (Open Biosystem) using Lipofectamine 2000 (Invitrogen) (Valier et al (2004) Stem Cells 22: 2-11). Stably transfected cells were then selected using puromycin and the resulting colonies were individually picked for further analyses. 100 hESC sublines (10 hESC sub-lines for each ShRNA expression vector) were analysed for the knock down of HEX and HLXB9 after differentiation into hepatic or pancreatic progenitor respectively. Further analyses were systematically performed on at least 2 hESCs sublines expressing different ShRNA sequences.

Animal Studies

Differentiated cells ($5 \times 10^6$) were grafted under the kidney capsule of NOD/SCID mice using a 24 G catheter attached to a positive displacement pipette. Blood samples were removed from the tail at various time intervals for C-peptide analysis. Kidneys were harvested at the indicated time points and a section containing the grafted cells fixed in 4% paraformaldehyde, wax embedded, and processed for immunohistochemistry. Antibody binding was visualised using 3,3'-diaminobenzidine (DAB).

Microarray Profiling

Total RNA was extracted using RNeasy® Mini Kit according to manufacturer's protocol (Qiagen). RNA samples were first assessed for their RNA integrity prior to hybridisation on the microarray. Five biological replicate samples for each condition among Day 4.5 and Day 4.5-Activin+SB differentiated hESCs were hybridised to Illumina Human HT-12 v4.0R1 Expression BeadChips using manufacturer's standard protocols. BeadChip probe-sets that did not pass the Illumina signal detection statistic at a threshold of $p<0.01$ in all sample replicates of at least one sample group were removed from further analysis. For all samples, the remaining probe-sets were background corrected, normalized and summarized using default parameters of the RMA model 23. Array processing was performed using the beadarray package of the Bioconductor suite of software for the R statistical programming language. Probe-sets were annotated using transcript information made available by the manufacturer. The raw microarray data described has been uploaded to the ArrayExpress repository (EBI) (Experiment name: Vallier hESC Endoderm. ArrayExpress accession: E-MEXP-2373 Analysis of Differential Regulation). The moderated t-statistic of 24, implemented in the limma package of Bioconductor, was employed to assess the significance of differential gene (probe-set) expression between sample groups. In order to reduce errors associated with multiple hypothesis testing on such a scale, the significance p-values obtained were converted to corrected q-values using the FDR method of 25. Probe-sets with associated $q<0.001$ (FDR 0.1%) were deemed to exhibit significant differential expression between sample groups. Data Visualisation: Heat maps of gene expression were created by importing relevant subsets of RMA processed microarray gene expression data into the Java Treeview data visualisation package. In the case wherein a gene is represented by more than one probe-set on the array, a single probe-set was chosen to represent gene expression in the heat map according to highest mean expression over all samples (i.e. the most reliable sample hybridization regardless of group membership). The raw microarray data described has been uploaded to the ArrayExpress repository (EBI).

Enzyme Linked Immunosorbent Assay (ELISA).

hESCs grown for 18 days in culture conditions inductive for pancreatic specification were cultured in differentiation medium without insulin for 24 h prior to Glucose stimulation. Cells were then washed three times in PBS and preincubated in DMEM supplemented with 2.2 mM glucose (Invitrogen) for 60 min at 37° C. To estimate glucose-induced insulin secretion, pre-incubated cells were grown in DMEM containing 22 mM glucose or alternatively 2.2 mM glucose for 15 or 60 minutes. Supernatants were collected for determination of C-peptide release. ELISA analyses were performed as followed. High binding surface COSTAR 96-well plates (Corning, N.Y., USA) were coated overnight with affinity purified rabbit polyclonal antibodies against al-antitrypsin (Abcam 31657, Cambridge, UK) and Albumin (Abcam 87564, Cambridge, UK) at 2 µg/ml in carbonate/bicarbonate buffer (Na2CO3/NAHCO3, pH 9.5). After washing (0.9% w/v NaCl, 0.05% v/v Tween 20), the plates were blocked for two hours in blocking buffer (PBS, 0.25% w/v BSA, 0.05% v/v Tween 20). Culture medium was diluted in blocking buffer and 50 µl added to each well then incubated for two hours. After washing, the wells were incubated with corresponding monoclonal antibodies (1 µg/ml diluted in blocking buffer), and incubated for two hours. Bound monoclonal antibodies were detected with rabbit anti-mouse IgG HRP-labelled antibody (Sigma Aldrich, Haverhill, UK, 1:20,000) for one hour. The reaction was developed with TMB liquid substrate (Sigma Aldrich, Haverhill, UK) for 10 minutes in the dark and the reaction was stopped with 1 M H2SO4. Absorbance was read at 450 nm on a Thermo-max microplate reader (Molecular Devices, Sunnyvale, Calif., U.S.A.).

Immunostaining hESCs or their differentiated progenitors were fixed for 20 minutes at 4° C. in 4% paraformaldehyde and then washed three times in PBS. Cells were incubated for 20 minutes at room temperature in PBST (0.1% Triton X100; Sigma; in PBS) containing 10% donkey serum (Serotec Ltd.) and subsequently incubated overnight at 4° C. with primary antibody (Table 11) diluted in 1% donkey serum in PBST. Cells were then washed three times in PBS and incubated with secondary antibodies (Table 11) in 1% donkey serum in PBST for 2 hours at room temperature. Unbound secondary antibody was removed by three 5 minutes washes in PBS. Hoechst 33258 was added to the first wash (Sigma-Aldrich; 1:10,000). For lipid visualization a lipid specific stain BODIPY (borondipyrromethene; BODIPY® 493/503 Invitrogen.D-3922) was used.

Flow Cytometry

Adherent cells at the specific stage of the pancreatic differentiation protocol were washed twice in PBS and then incubated for 20 minutes at 37° C. in cell dissociation buffer (Invitrogen, Carlsbad, Calif.). Cells were dissociated by gentle pipetting and resuspended at approximately 0.1-1× 105 cells per milliliter in PBST+3% normal donkey serum (NDS) containing 0.1% azide (Serotec Ltd., Oxford, U.K.). Cells were then fixed for 20 minutes at 4° C. in 4% paraformaldehyde and then washed three times in PBS. Cells were pelleted and resuspended in 2 mL of SAP buffer (0.1% (w/v) saponin In Hanks' Balanced Salt Solution). Cells were incubated for 2 hours at room temperature with primary antibody (Table 11) in SAP buffer. Cells were then washed three times in PBS+3% NDS and then incubated with secondary antibodies (Table 11) in SAP buffer for 2 hours at room temperature. Unbound secondary antibody was removed by three washes in PBS. Cells were then analyzed using a FACS Calibur machine (BD Biosciences, San Jose, Calif., USA). Number of positive cells was recorded as the average from three separate experiments.

Results

Inhibition of Activin and BMP Signalling in the Presence of Retinoic Acid Induces PDX1 Expression in hESC Derived Endoderm Cells Grown in Fully Defined Culture Conditions.

We recently established a defined culture system to differentiate hESCs and hIPSCs into near homogenous populations of Definitive Endoderm (DE) cells (Teo A K et al. (2011) Genes Dev 25: 238-250). Importantly, this culture system relies on a chemically defined medium (CDM) devoid of animal products, including BSA, serum, complex extra cellular matrix such as Matrigel™, or feeders cells; thereby avoiding the presence of unknown factors which could interfere with experimental outcomes. To further extend this protocol, we screened a broad number of combinations of growth factors and inhibitors of signalling pathways to identify defined culture conditions driving differentiation of DE cells into pancreatic progenitors. These analyses revealed that a combination of RA, FGF10, Noggin (BMP inhibitor) and SB431542 (Activin/TGFβ receptor antagonist) was able to induce the expression of the pancreatic markers PDX1, HNF6, PTF1A, Sox9 and HLXB9 while inhibiting the expression of gut (CDX2) and liver markers (AFP) in hESC derived DE cells (FIG. 2). Importantly, this cocktail of factors only induced PDX1 in specific basal medium (Advanced DMEM) while the presence of serum, Matrigel™ or feeders inhibited pancreatic progenitor differentiation confirming that DE differentiation can be influenced by a diversity of factors. We then sought to validate and optimise the role of each of these additives. Absence of RA in the presence of Noggin, FGF10, and SB431542 (SB) inhibited the expression of pancreatic markers (FIG. 2) confirming that RA is necessary for the induction of pancreatic specification (Mfopou J K et al (2010) Gastroenterology 138: 2233-2245, 2245 e2231-2214). Absence of Noggin or addition of BMP4 at any time during the differentiation process (FIG. 2) resulted in a significant decrease in the expression of pancreatic progenitor markers while inducing gut (CDX2) and liver markers (AFP) thereby reinforcing previous studies showing that BMP signalling inhibits pancreatic specification to promote alternative cell fate (Cai J et al. (2010). J Mol Cell Biol 2: 50-60). Inhibition of FGF signalling using SU5402 (FGF receptor antagonist) or increasing dose of FGF2/7/10 did not affect the expression of pancreatic progenitor markers such as PDX1, SOX9 and HLXB9 (FIG. 2). However, the expression of the gut marker CDX2 (Wells et al (2000) Development 127: 1563-1572) was augmented while expression of PTF1A was strongly reduced in the absence of FGF signalling suggesting that FGF10 could block the specification of PDX1 expressing cells toward duodenum (Wells et al (2000), Spence et al (2011) Nature 470: 105-109) during pancreatic bud specification. Furthermore, FGF inhibition caused significant cell death, implying that FGFs were also necessary for proliferation and survival of pancreatic progenitor in vitro. More importantly, we observed that addition of Activin abolished the expression of pancreatic markers while inhibition of Activin/TGFβ signalling by SB had the opposite effect (FIG. 2), demonstrating for the first time that Activin/TGFβ signalling inhibits pancreatic specification in vitro.

Interestingly, the presence of SB was only required for the first 3 days of differentiation indicating that Activin/TGFβ signalling acted on the earliest steps of pancreatic specification preceding PDX1 expression. Together these results show that RA acts as an inductive signal driving differentiation of DE cells toward the pancreatic lineage while TGFβ signalling pathways (i.e. Activin+BMP) act as a potent inhibitor of this cell fate choice.

Figure 1:
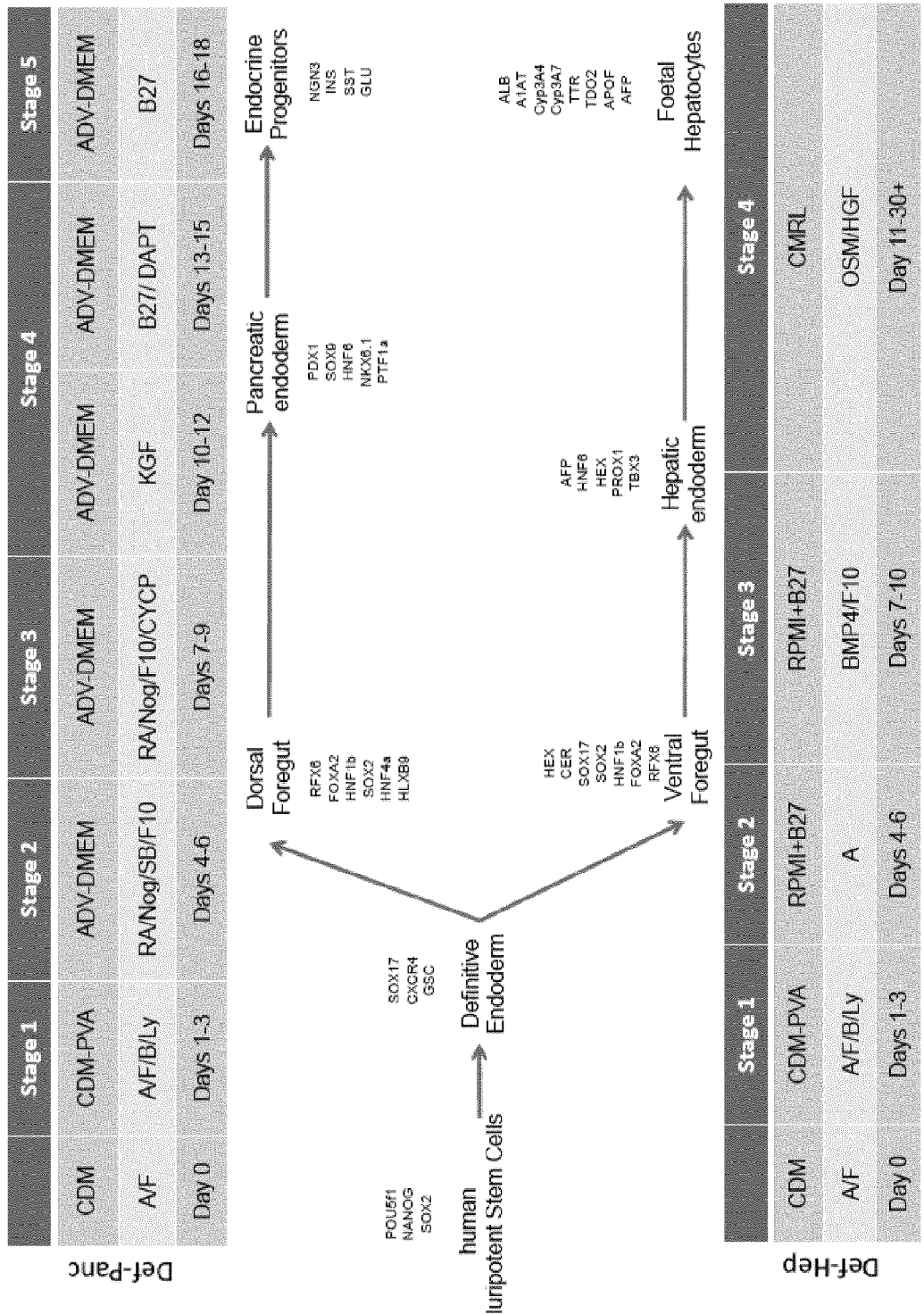
FIG. 1 shows protocols to generate hepatic and pancreatic progenitor from hESCs and hIPSCs.

Inhibition of Activin/TGFβ Induces Differentiation of Endoderm into a Near Homogenous Population of Pancreatic Progenitor Following a Native Path of Development Based on the results described above, we established a 4 step protocol to differentiate hESCs into pancreatic progenitor using defined culture media (Def-Panc, FIG. 1). During the first step (Day 1-3), hESCs were grown in CDM supplemented with Activin/BMP/FGF2/LY294002 (PI 3-K inhibitor) (Teo et al (2011)). The resulting cells were positive for the expression of DE markers including SOX17, CXCR4, HEX, FOXA2 and EOMES whilst simultaneously negative for expression of the pluripotency markers OCT-4, NANOG and SOX2 and the primitive streak markers T (Brachyury) and Mixl1 (FIG. 3). The second step of the Def-Panc protocol involved growing DE cells in the presence of RA/Noggin/FGF10/SB431542 for 3 days (Day 4-6). The resulting cells expressed HNF1β, FOXA2, HNF4, RFX6 and HLXB9 (FIG. 4), all of which mark the foregut during early mammalian development (FIG. 3). Notably, the expression of HLXB9 and the absence of HEX expression provided indication of a dorsal identity for these foregut cells, while the absence of CDX2 excluded the presence of midgut or hindgut cells (FIG. 3). In the third step of the protocol, dorsal foregut cells were grown for 3 additional days in the presence of RA/Noggin/FGF10/Cyclopamine (Day 7-9). The resulting cells expressed a combination of foregut markers (HNF1β, SOX2, FOXA2, and HLXB9) and pancreatic progenitor markers (SOX9, HNF6, PTF1A and PDX1) (FIG. 3). The expression of pancreatic progenitor markers was further reinforced in the fourth step of the protocol by addition of FGF10 for 3 days (Day 10-12). The resulting cells expressed NKX6.1, SOX9, HNF6, PTF1A, PDX1, HNF1β, SOX2, and FOXA2 while the expression of HLXB9 was strongly diminished (FIG. 3). FACS analyses performed at the end step 1 showed that the DE enriched cells were homogeneously positive for CXCR4 and after the fourth step of the protocol (Day 12) 80% of the cells expressed PDX1 (FIG. 4). Immunostaining analyses confirmed that PDX1 was co-expressed in the same cells with SOX9, HNF6, HNF4, NKX6.1 and GATA4. Together these results indicated that the Def-Panc protocol drives differentiation of hESCs toward a near homogenous population of pancreatic progenitor cells following successive events of specifications reminiscent of those that occur during pancreatic development.

PDX1 Endoderm Generated in Defined Culture Conditions can Differentiate into Insulin Secreting Cells In Vitro and In Vivo.

To confirm the capacity of pancreatic progenitor cells to differentiate further toward the endocrine lineage, PDX1 expressing cells obtained at the end of stage 4 were grown for 6 additional days in culture conditions previously shown to stimulate endocrine cells differentiation (Kroon E et al. (2008) Nat Biotechnol 26: 443-452). Q-PCR analyses showed that PDX1 expression decreased after 3 days while expression of NGN3 and hormonal markers (insulin, glucagon and somatostatin) progressively increased (FIG. 3). By Day 18, 10% of cells stained positive for C-peptide.

Interestingly, these hESC-derived insulin-expressing cells were able to release C-peptide upon glucose stimulation mimicking insulin release by β-cells (FIG. 5). Nonetheless, expression of hormonal markers (Insulin, SST and GSC) was relatively low when compared to human adult Islets cells while expression of markers specific for pancreatic endocrines was maintained (NKX6.1, NGN3, and Sox9).

Furthermore, a fraction of C-peptide expressing cells were also found to be positive for glucagon or somatostatin (Poly-hormonal expression could mark β cells of embryonic origin (Polak M et al (2000) Diabetes 49: 225-232) thereby confirming that our in vitro culture conditions are not sufficient to generate fully functional endocrine cells. To overcome this limitation of in vitro system, pancreatic progenitor cells obtained after 12 days of differentiation were injected under the kidney capsule of NOD-SCID mice to provide an environment known to favour their differentiation into endocrine cells (Kroon E et al. (2008) Nat Biotechnol 26: 443-452). Low levels of human C-peptide were detected in the blood stream of 3 out of 8 transplanted animals as soon as 12 weeks after transplantation (negative control=0.021 ng/ml; mouse 1=0.1 ng/ml, mouse 2=0.43 ng/ml, and mouse 3=0.1635 ng/ml). In addition, histology analyses of pancreatic markers in kidney capsule of mouse engrafted with pancreatic progenitor cells performed after 20 weeks of differentiation in vivo revealed the presence of Islet looking like clusters with cells expressing glucagon and C-Peptide.

Together, these results demonstrate that pancreatic progenitor cells generated with the Def-Panc protocol have the capacity to differentiate further into endocrine cells and thus represent early pancreatic progenitors. Finally, similar results were obtained with 3 hIPSCs lines indicating that the Def-Panc protocol could be used successfully to produce pancreatic progenitors from diverse hPSCs.

Activin/TGFβ Drives Differentiation of Endoderm Cells into Hepatic Progenitors which can Differentiate into Foetal Hepatocytes During the screening of the culture conditions described above, we noted that DE cells grown in the presence of Activin acquired the appearance of foetal hepatocytes with large darkened cytoplasmic space and canaliculi-like structures. Further analyses confirmed that DE cells grown in the presence of Activin for 5 days expressed genes marking ventral foregut, the site of liver bud formation (HEX, SOX17, HNF4, FOXA1, FOXA2, TBX3 in FIG. 7). Conversely, inhibition of Activin by SB decreased the expression of HNF4α, SOX17, HEX and TBX3, while blocking known hepatic inducers such as FGF signalling also decreased the expression of liver bud genes such as HEX, Sox17 and TBX3 (FIG. 8). Surprisingly, Noggin only induced a moderate decrease in HNF4 expression providing indication that BMP signalling might have a limited function in hepatic specification in vitro. Alternatively, unknown signaling pathways could activate the same program of differentiation. Considered together, these results suggest that combined effect of Activin, BMP and FGF is necessary to fully promote hepatic specification of DE cells in vitro.

Based on this observation, we developed a 3 steps protocol to generate hepatocytes from hPSCs in defined culture conditions (Def-Hep, FIG. 1). The first step of the Def-Hep protocol consists in differentiating hESCs into DE cells as described above while the second steps involved promoting DE specification toward the hepatic lineage using first Activin alone for 3 days and then Activin combined with BMP4 and FGF10. In the third step of the Def-Hep protocol, hepatic endoderm cells were grown for 15 additional days in the presence of Oncostatin M and HGF, two growth factors known to control hepatoblast differentiation into hepatocytes.

Accordingly, the cells generated with the Def-Hep protocol express hepatocyte markers such as albumin (ALB), α-1-antitrypsin (AAT), αAPOF, TAT, TDO2, TTR, HNF4α and HEX (FIG. 9). These observations were confirmed by immunostaining and FACS analyses, which showed homogenous co-expression of ALB, cytokeratin18, AAT and AFP (FIG. 10). These cells also displayed functional characteristic of hepatocytes such as: (i) ALB and AAT secretion (FIG. 11), (ii) Cyp3A4 activity inducible by dexamethasone (FIG. 12), (iii) cholesterol uptake (as shown by a a DIL assay) and (iv) glycogen storage (as shown by PAS staining). Together, these data demonstrate that Activin drives DE specification toward VF like cells and then hepatic endoderm, which has the capacity to differentiate into cells displaying characteristic of foetal hepatocytes.

HEX and HLXB9 Knock Down During Pancreatic and Hepatic Differentiation of hESCs Block Respectively Hepatic and Pancreatic Differentiation.

We then decided to take advantage of the Def-Panc and Def-Hep culture systems to study the mechanisms by which Activin can control the cell fate choice between the pancreatic and hepatic lineages. For that, we performed gene expression profiling experiments to identify genes that were up or down regulated by the presence of Activin during pancreatic specification. These analyses of DE cells grown for 36 hours in the presence Activin/RA/Nog/FGF (D45A) or SB/RA/Nog/FGF (D45SB) revealed that Activin could activate or block the expression of a broad number of genes including HEX and HLXB9, which are known to be essential for foregut development. Thus, we hypothesised that Activin could direct DE specification by controlling the expression of these transcription factors. To test this hypothesis, we knocked down HEX or HLXB9 expression in hESCs using stable expression of ShRNA. The resulting hESC sub-lines (ShHEX-hESCs and ShHLXB9-hESCs) were then differentiated as described in FIG. 1. Q-PCR analyses showed that knock down in HEX expression during DE differentiation (FIG. 13) was systematically associated with down regulation of hepatic markers such as AFP and ALB (FIG. 14). A similar decrease was not observed with DE cells derived from ShHLXB9-hESCs hESCs or DE cells derived from hESCs stably overexpressing a non-targeting ShRNA (ShScramble-hESCs). However, we also observed that reduced HEX expression increase cell death during VF differentiation (FIG. 15). Therefore, HEX expression appears to be necessary for survival and differentiation of VF like cells toward the hepatic lineage in vitro. Finally, ShHEX-hESCs were able to differentiate into pancreatic progenitor expressing successively HLXB9 and PDX1 (FIG. 16).

Similar experiments performed with ShHLXB9-hESCs showed that knock down in HLXB9 expression during foregut differentiation strongly decreased the expression of pancreatic progenitor markers including PDX1/SOX9 (FIG. 17). Interestingly, a decrease in HLXB9 expression did not affect the expression of foregut makers such as HNF4α, FoxA2 and HNF1β (FIG. 17), providing indication that HLXB9 is not required for dorsal foregut specification while being necessary for its differentiation toward the pancreatic lineage. Importantly, HLXB9 is not expressed during hepatic differentiation (FIG. 18) and thus DE cells generated from ShHLXB9-hESCs were able to differentiate into VF like cells and into hepatic endoderm when grown in the presence of Activin. Collectively these results recapitulate studies performed in the mouse embryo showing that absence of HEX disrupts hepatic bud development without affecting dorsal pancreatic specification while HLXB9 is necessary for the induction of PDX1 expression in the pancreas (Habener J F, et al (2005) Endocrinology 146: 1025-1034). Therefore, they demonstrate the general application of our culture system in modelling DE development and studying early organogenesis of pancreas and liver in vitro.

Robust protocols allowing for the production of homogenous populations of liver and pancreatic progenitors from hPSCs under culture conditions compatible with clinical applications have not yet been established. Indeed, available methods often contain undefined animal products such as feeders or foetal bovine serum (FBS). To address these challenges, we identified defined culture conditions to differentiate human definitive endoderm (DE) into a near homogeneous population of pancreatic and liver endoderm from multiple hPSC lines.

RA was found to have an essential function in promoting pancreatic specification while BMP signalling blocks the expression of the pancreatic marker PDX1 reinforcing previous studies (Mfopou et al (2010) Gastroenterology 138: 2233-2245, 2245 e2231-2214; [Cai et al (2010 J Mol Cell Biol 2: 50-60). However, our results concerning the function of FGF signalling contradict previous studies (Ameri J et al. (2010) Stem Cells 28: 45-56) by indicating that FGF acts as a permissive signal rather than an inductive signal of pancreatic specification. This apparent divergence might be explained by the absence in our culture conditions of feeders, serum and Matrigel™ all of which contains unknown components that are prone to interfere with FGF signalling.

In addition, we observed that inhibition of FGF signalling decreases cells survival of pancreatic progenitors, thus justifying the use of FGFs in our protocol. More importantly, our analyses also revealed that Activin/TGFβ controls DE cell fate choice toward the pancreas lineage by inhibiting dorsal foregut (DF) specification while promoting the hepatic lineage. Previous studies have shown that TGFb signalling controls ventral pancreatic bud induction in mouse embryo (Wandzioch E, Zaret K S (2009) Science 324: 1707-1710) and thus, our data demonstrate for the first time that similar mechanisms could occur in the dorsal pancreas confirming the interest of our culture system to model foregut development in vitro.

Finally, these results have important practical significance since protocols currently available to generate pancreatic cells from hPSCs often rely on feeders, Matrigel™ and serum all which represent potential source of TGFβ signalling with the capacity to compromise pancreatic specification. Moreover, recent studies have shown that endogenous level of Nodal expression could determine the capacity of specific hIPSC lines to differentiate into mesodermal derivatives (Ramos-Mejia V, Melen G J, Sanchez L, et al. (2010). Mol Ther 18: 2173-2181). Such differences in endogenous level of Nodal/TGFβ growth factors could affect the capacity of diverse hPSCs lines to differentiate into pancreatic progenitor and the inhibition of this signalling pathway with SB could bypass this limitation. Accordingly, we recently differentiated 10 hIPSC lines into pancreatic progenitor using our 4 steps protocol and we observed that only those hIPSCs lines that failed to differentiate into DE (2 out of 10) also lack the ability to differentiate into pancreatic cells. Another advantage of inhibiting TGFβ signalling during DE differentiation resides in the possibility of eliminating contaminating pluripotent cells. Indeed, we and others have extensively demonstrated that inhibition of Activin/Nodal/TGFβ signalling induced differentiation of hPSCs (Vallier L et. al. (2009) Development 136: 1339-1349). Thus, inhibition of Activin during DE specification could decrease contamination by undifferentiated cells. Accordingly, we never observed teratoma formation in mice transplanted with pancreatic progenitors. Therefore, inhibiting Activin signalling during pancreatic specification may allow the generation of "safer" pancreatic progenitor for potential cell based therapy.

To conclude, our study could greatly facilitate the production of homogenous population of pancreatic and liver cells in defined culture conditions for clinical applications. However, this culture system also provides a robust and efficient in vitro model of development to study human endoderm differentiation.

| Components | Molecular Weight | Concentration (mg/L) | mM |
|---|---|---|---|
| Amino Acids | | | |
| Glycine | 75 | 37.5 | 0.5 |
| L-Alanine | | 8.9 | ∞ |
| L-Arginine hydrochloride | | 84 | ∞ |
| L-Asparagine | | 13.2 | ∞ |
| L-Aspartic acid | | 13.3 | ∞ |
| L-Cystine 2HCl | | 63 | ∞ |
| L-Glutamic Acid | | 14.7 | ∞ |
| L-Histidine hydrochloride-H2O | | 42 | ∞ |
| L-Isoleucine | | 105 | ∞ |
| L-Leucine | | 105 | ∞ |
| L-Lysine hydrochloride | | 146 | ∞ |
| L-Methionine | | 30 | ∞ |
| L-Phenylalanine | | 66 | ∞ |
| L-Proline | | 11.5 | ∞ |
| L-Serine | | 52.5 | ∞ |
| L-Threonine | | 95 | ∞ |
| L-Tryptophan | | 16 | ∞ |
| L-Tyrosine disodium salt dihydrate | | 104 | ∞ |
| L-Valine | | 94 | ∞ |
| Vitamins | | | |
| Ascorbic Acid phosphate | | 2.5 | ∞ |
| Choline chloride | | 4 | ∞ |
| D-Calcium pantothenate | 477 | 4 | 0.00839 |
| Folic Acid | 441 | 4 | 0.00907 |
| Niacinamide | | 4 | ∞ |
| Pyridoxine hydrochloride | | 4 | ∞ |
| Riboflavin | | 0.4 | ∞ |
| Thiamine hydrochloride | | 4 | ∞ |
| i-Inositol | | 7.2 | ∞ |
| Inorganic Salts | | | |
| Calcium Chloride (CaCl2) (anhyd.) | 111 | 200 | 1.8 |
| Ferric Nitrate (Fe(NO3)3"9H2O) | | 0.1 | ∞ |
| Magnesium Sulfate (MgSO4) (anhyd.) | | 97.67 | ∞ |
| Potassium Chloride (KCl) | | 400 | ∞ |
| Sodium Bicarbonate (NaHCO3) | | 3700 | ∞ |
| Sodium Chloride (NaCl) | | 6400 | ∞ |
| Sodium Phosphate dibasic (Na2HPO4—H2O) | | 125 | ∞ |
| Proteins | | | |
| AlbuMAX ® II | | 400 | ∞ |
| Human Transferrin (Holo) | | 7.5 | ∞ |
| Insulin Recombinant Full Chain | | 10 | ∞ |
| Trace Elements | | | |
| Ammonium Metavanadate | | 0.0003 | ∞ |
| Cupric Sulfate | | 0.00125 | ∞ |
| Manganous Chloride | | 0.00005 | ∞ |
| Sodium Selenite | | 0.005 | ∞ |
| Other Components | | | |
| D-Glucose (Dextrose) | | 4500 | ∞ |
| Ethanolamine | | 1.9 | ∞ |
| Glutathione (reduced) | 307 | 1 | 0.00326 |
| Phenol Red | | 15 | ∞ |
| Sodium Pyruvate | | 110 | ∞ |

REFERENCES

[1] Thomson J A et al (1998) Science 282: 1145-1147
[2] Takahashi K, Tanabe K, Ohnuki M, et al. (2007) Cell 131: 861-872
[3] D'Amour K A, et al. (2006) Nat Biotechnol 24: 1392-1401
[4] Jiang W, et al. (2007). Cell Res 17: 333-344
[5] Maehr R, et al. (2009) Proc Natl Acad Sci USA 106: 15768-15773
[6] Zhang D, Jiang N, Liu M, et al. (2009) Cell Res 19:429-438
[7] Kroon E, et al. (2008) Nat Biotechnol 26: 443-452
[8] Kelly O G, et al. (2011) Nat Biotechnol 29: 750-756
[9] Zaret K S, Grompe M (2008) Science 322: 1490-1494
[10] Harrison K A, et al (1999) Nat Genet 23: 71-75
[11] Li H, et al (1999) Nat Genet 23: 67-70
[12] Jonsson J, et al (1994) Nature 371: 606-609
[13] Offield M F, et al. (1996) Development 122:983-995
[14] Sherwood R I, et al (2009) Dev Dyn 238: 29-42
[15] Wandzioch E, Zaret K S (2009). Science 324: 1707-1710
[16] Rashid S T et al. (2010) J Clin Invest 120: 3127-3136
[17] Brons I G et al. (2007) Nature 448: 191-195
[18] Touboul T, et al. (2010) Hepatology 51: 1754-1765
[19] Vallier L, et al (2004) Stem Cells 22: 2-11
[20] Teo A K, et al. (2011) Genes Dev 25: 238-250
[21] Mfopou J K et al (2010) Gastroenterology 138: 2233-2245,
[22] Cai J, et al. (2010) J Mol Cell Biol 2:50-60
[23] Wells J M, Melton D A (2000) Development 127: 1563-1572
[24] Spence J R et al. (2011) Nature 470: 105-109
[25] Polak M, et al (2000) Diabetes 49: 225-232
[26] Habener J F, et al (2005) Endocrinology 146: 1025-1034
[27] Ameri J, et al. (2010) et al. Stem Cells 28: 45-56
[28] Nostro M C, et al, et al. (2011) Development 138: 861-871
[29] Kunisada Y, et al (2012) Stem Cell Res 8: 274-284
[30] Brown S et al. (2011) Stem Cells 29: 1176-1185
[31] Inamura M et al. Mol Ther 19: 400-407
[32] Bort R et al (2004) Development 131: 797-806
[33] Kubo A, et al. (2009) Hepatology 51: 633-641
[34] Ramos-Mejia V et al. (2010) Mol Ther 18: 2173-2181
[35] Vallier L et al. (2009) Development 136: 1339-1349

The invention claimed is:

1. A method for producing a population of pancreatic progenitor cells which comprises:
   i) providing a population of pluripotent cells;
   ii) culturing the population in a definitive endoderm (DE) induction medium to produce a population of definitive endoderm cells, wherein the definitive endoderm (DE) induction medium comprises a TGFβ ligand, fibroblast growth factor (FGF), bone morphogenetic protein (BMP), a PI3K inhibitor and a GSK3β inhibitor;
   iii) culturing the population of definitive endoderm cells in a first pancreatic induction medium comprising an activin antagonist; FGF; retinoic acid; and a BMP inhibitor to produce a population of dorsal foregut cells;
   iv) culturing the dorsal foregut cells in a second pancreatic induction medium comprising FGF, retinoic acid, a BMP inhibitor, and a hedgehog signalling inhibitor;
   v) culturing the cells produced in step (iv) in a third pancreatic induction medium comprising FGF;
   thereby producing a population of pancreatic progenitor cells.

2. A method according to claim 1 wherein the definitive endoderm (DE) induction medium is a chemically defined medium which comprises TGFβ ligand, fibroblast growth factor (FGF), bone morphogenetic protein (BMP) and a PI3K inhibitor.

3. A method according to claim 2 wherein the definitive endoderm (DE) induction medium is a chemically defined medium which consists of a basal medium supplemented with activin, fibroblast growth factor (FGF), bone morphogenetic protein (BMP) and LY294002.

4. A method according to claim 3 wherein the pluripotent cells are cultured in said DE induction medium for 2 to 4 days to produce the population of definitive endoderm cells.

5. A method according to claim 1 wherein step (ii) comprises:
   (a) culturing the population of pluripotent cells in said DE induction medium,
   (b) further culturing the population in another definitive endoderm induction medium lacking GSK3β inhibitor; and
   (c) further culturing the population in an anterior definitive endoderm (ADE) induction medium which comprises a TGFβ ligand and fibroblast growth factor.

6. A method according to claim 5 wherein the ADE induction medium is a chemically defined medium which consists of a basal medium supplemented with activin and fibroblast growth factor (FGF).

7. A method according to claim 5 wherein the population is cultured for 24 hours in each of steps a) to c).

8. A method according to claim 1 wherein the definitive endoderm cells express SOX17, CXCR4 and GSC.

9. A method according to claim 1 wherein the first pancreatic induction medium is a chemically defined medium which comprises activin/TGFβ antagonist; FGF; retinoic acid; and a BMP antagonist.

10. A method according to claim 9 wherein the first pancreatic induction medium is a chemically defined medium which consists of a basal medium supplemented with SB-431542; FGF; retinoic acid; and noggin.

11. A method according to claim 1 wherein the dorsal foregut cells express RFX6, FOXA2, HNF1b, SOX2, HNF4a, and HLXB9.

12. A method according to claim 1 wherein the second pancreatic induction medium is a chemically defined medium which comprises FGF, a BMP antagonist, retinoic acid, and a hedgehog signalling inhibitor.

13. A method according to claim 12 wherein second pancreatic induction medium is a chemically defined medium which consists of a basal medium supplemented with FGF; retinoic acid; noggin; and KAAD-cyclopamine.

14. A method according to claim 1 wherein the third pancreatic induction medium is a chemically defined medium which comprises FGF.

15. A method according to claim 14 wherein third pancreatic induction medium is a chemically defined medium which consists of a basal medium supplemented with FGF.

16. A method according to claim 14 wherein the third pancreatic induction medium further comprises retinoic acid.

17. A method according to claim 1 wherein the pancreatic progenitor cells express PDX1, SOX9, HNF6, NKX6.1 and PTF1a.

18. A method according to claim 1 comprising maturing the pancreatic progenitor cells to produce a population of pancreatic endocrine cells.

19. A method according to claim 18 wherein the pancreatic progenitor cells are matured by i) culturing in a first endocrine induction medium and ii) culturing in a second endocrine induction medium to produce the population of pancreatic endocrine cells,
   wherein the first endocrine induction medium is a chemically defined medium comprising a Notch signalling inhibitor; and the second endocrine induction medium is a chemically defined medium devoid of differentiation factors.

20. A method according to claim 19 wherein the first endocrine induction medium is a chemically defined medium consisting of a supplemented basal medium and N—[N-(3,5-difluorophenacetyl)-1-alanyl]-S-phenylglycine t-butyl ester (DAPT); and the second endocrine induction medium is a chemically defined medium consisting of a supplemented basal medium.

21. A method according to claim 18 wherein the pancreatic progenitor cells are matured by i) culturing in a first endocrine induction medium and ii) culturing in a second endocrine induction medium to produce the population of pancreatic endocrine cells,
   wherein the first endocrine induction medium is a chemically defined medium comprising a Notch signalling inhibitor and retinoic acid; and the second endocrine induction medium is a chemically defined medium devoid of differentiation factors other than retinoic acid.

22. A method according to claim 21 wherein the first endocrine induction medium is a chemically defined medium consisting of a supplemented basal medium, N—[N-(3,5-difluorophenacetyl)-1-alanyl]-S-phenylglycine t-butyl ester (DAPT) and retinoic acid; and the second endocrine induction medium is a chemically defined medium consisting of a supplemented basal medium and retinoic acid.

23. A method according to claim 18 wherein the pancreatic endocrine cells express NGN3, INS, SST and GLU.

24. A method according to claim 1 comprising monitoring and/or detecting the expression of one or more cell markers in the population of differentiating cells.

25. A method according to claim 1 comprising expanding the population of pancreatic progenitor cells.

26. A method according to claim 1 comprising culturing or maintaining the population of pancreatic progenitor cells.

27. A method according to claim 1 comprising storing the population of pancreatic progenitor cells.

28. A method according to claim 1 comprising admixing the population of pancreatic progenitor cells with a therapeutically acceptable excipient.

29. A method according to claim 1 wherein the pluripotent cells are human pluripotent cells.

30. A method according to claim 1 wherein the pluripotent cells are ESCs or iPSCs.

31. A method according to claim 30 wherein the pluripotent cells are iPS cells derived from an individual with a genetic background associated with a pancreatic condition.

32. A method according to claim 31 wherein the pluripotent cells are iPS cells derived from an individual with a genetic disorder associated with a pancreatic condition.

33. A method according to claim 18 comprising expanding the population of pancreatic endocrine cells.

34. A method according to claim 18 comprising culturing or maintaining the population of pancreatic endocrine cells.

35. A method according to claim 18 comprising storing the population of pancreatic endocrine cells.

36. A method according to claim 18 comprising admixing the population of pancreatic endocrine cells with a therapeutically acceptable excipient.

37. A method according to claim 2 wherein the DE induction medium is a chemically defined medium which consists of a basal medium supplemented with activin, fibroblast growth factor (FGF), bone morphogenetic protein (BMP), LY294002 and CHIR99021.

38. A method according to claim 37 wherein the pluripotent cells are cultured in said DE induction medium for 2 to 4 days to produce the population of DE cells.

39. A method according to claim 14 wherein third pancreatic induction medium is a chemically defined medium which consists of a basal medium supplemented with FGF and retinoic acid.

\* \* \* \* \*